(12) United States Patent
Zerangue

(10) Patent No.: US 7,462,459 B2
(45) Date of Patent: Dec. 9, 2008

(54) LAT1 TRANSPORTERS EXPRESSED IN BLOOD BRAIN BARRIER CELLS

(75) Inventor: Noa Zerangue, Sunnyvale, CA (US)

(73) Assignee: XenoPort, Inc., Santa Clara, CA (US)

( * ) Notice: Subject to any disclaimer, the term of this patent is extended or adjusted under 35 U.S.C. 154(b) by 484 days.

(21) Appl. No.: 11/027,767

(22) Filed: Dec. 30, 2004

(65) Prior Publication Data

US 2005/0201931 A1 Sep. 15, 2005

Related U.S. Application Data

(60) Provisional application No. 60/540,754, filed on Jan. 30, 2004.

(51) Int. Cl.
G01N 33/53 (2006.01)
C07K 14/00 (2006.01)
C07H 21/04 (2006.01)

(52) U.S. Cl. .......................... 435/7.1; 435/7.2; 435/7.3; 435/69.1; 435/235.1; 435/320.1; 435/325; 530/350; 536/23.1; 536/23.5

(58) Field of Classification Search .................. None
See application file for complete search history.

(56) References Cited

U.S. PATENT DOCUMENTS 6,489,302 B1 12/2002 Wiessler et al.

2003/0158254 A1 8/2003 Zerangue et al.

OTHER PUBLICATIONS

Alderman, D.A.; "A Review of Cellulose Ethers in Hydrophilic Matrices for Oral Controlled-Release Dosage Forms"; *Int. J. Pharm. Tech. & Prod. Mfr.* 5(3):1-9 (1984).
Altschul, S. et al.; "Basic Local Alignment Search Tool"; *J. Mol. Biol.* 215:403-410 (1990).
Audus, K. et al.; Characterization of an in vitro blood-brain barrier model system for studying drug transport and metabolism, *Pharmaceutical Res.* 3(2):81-87 (1986)).
Audus, K. et al.; The use of cultured epithelial and endothelial cells for drug transport and metabolism studies, *Pharmaceutical Res.* 7(5):435-451 (1990)).
Bamba, M. et al.; "Release Mechanisms in Gelforming Sustained Release Preparations"; *Int. J. Pharmaceuticals* 2:307-315 (1979).
Bowman, P. et al.; "Brain microvessel endothelial cells in tissue culture: A model for study of blood-brain barrier permeability"; *Ann. Neurol.* 14:396-402 (1983).
Brightman and Neuwelt (ed.); Implications of the blood-brain barrier and its manipulation; vol. 1, Plenum Medical, New York, pp. 53-83 (1989).

(Continued)

*Primary Examiner*—Gary B. Nickol
*Assistant Examiner*—Nirmal S Basi
(74) *Attorney, Agent, or Firm*—Townsend and Towsend and Crew LLP

(57) ABSTRACT

LAT1 is consistently expressed at high levels in brain microvessel endothelial cells. Disclosed herein are assays for determining whether a test material/molecule is a substrate for, and/or is actively transported by, the LAT1 transporter, and therefore a candidate substrate for crossing the blood brain barrier. The assays are useful in screening for therapeutic, cytotoxic or imaging compounds used in the treatment or diagnosis of neurological diseases.

18 Claims, 13 Drawing Sheets

LAT1 SUBSTRATES

Tryptophan

Phenylalanine

Gabapentin

Leucine

Bicyclohexane amino acid

Baclofen

Methionine

L-dopa

OTHER PUBLICATIONS

Cserr, H. et al.,; "Blood-brain interfaces in vertebrates: a comparative approach"; *Am. J. Physiol. Regulatory, Integrative and Comparative Physiology* 246:277-288 (1984).

During, M. et al.; "Controlled Release of Dopamine from a Polymeric Brain Implant: In Vivo Characterization"; *Ann. Neurol.* 25:351-356 (1989).

Goldstein, G. et al.; "The Blood-Brain Barrier"; *Scientific American* 255(3):74-83 (1986).

Hanes, J. et al.; "New Advances in Microsphere-Based Single-Dose Vaccines"; *Advanced Drug Delivery Reviews* 28:97-119 (1997).

Henikoff, S. et al.; Amino Acid Substitution Matrices from Protein Blocks; *Proc. Natl. Acad. Sci. USA* 89:10915-19 (1989).

Howard, M. et al.; "Intracerebral Drug Delivery in Rats with Lesion-Induced Memory Deficits"; *J. Neurosurg.* 71:105-112 (1898_).

Karlin, S. et al.; "Applications and Statistics for Multiple High-Scoring Segments in Molecular Sequences"; *Proc. Nat'l. Acad. Sci. USA* 90:5873-87 (1993).

Langer, R.; "New Methods of Drug Delivery"; *Science* 249:1527-1533 (1990).

Langer, R. et al.; "Chemical and Physical Structure of Polymers as Carriers for Controlled Release of Bioactive Agents: A Review"; *J. Macromol. Sci. Rev. Macromol Chem.* 23:61-126 (1983).

Levy, R. et al.; "Inhibition of Calcification of Bioprosthetic Heart Valves by Local Controlled-Release Diphosphonate"; *Science* 228:190-193 (1985).

Masereeuw, R. et al.; "In vitro and in vivo transport of zidovudine (AZT) across the blood-brain barrier and the effect of transport inhibitors"; *Pharm. Res.* 11(2):324-330 (1994).

Meresse, S. et al.; "Bovine brain endothelial cells express tight junctions and monoamine oxidase activity in long-term culture"; *J. Neuorchem.* 53:1363-1371 (1989).

Needleman, S. et al.; "A General Method Applicable to the Search for Similarities in the Amino Acid Sequence of Two Proteins"; *J. Mol. Biol.* 48:443-453 (1970).

Pardridge, W. M.; "Receptor-Mediated Peptide Transport Through the Blood-Brain Barrier"; (1986) *Endocrine Rev.* 7(3):314-330 (1986).

Pardridge, W. M. et al.; "Comparison of in vitro and in vivo models of drug transcytosis through the blood-brain barrier"; *J. Pharmacol. Exp. Thera.* 253(2):884-891 (1990).

Pearson, W. et al.; "Improved Tools for Biological Sequence Comparison"; *Proc. Nat'l Acad. Sci. USA* 85:2444-48 (1988).

Smith, T. et al.; "Comparison of Biosequences"; *Adv. Appl. Math.* 2:482-489 (1981).

Terasaki, T. et al.; "New Approaches to in vitro Models of Blood-Brain Barrier Drug Transport"; *Drug Discovery Today* 8:944-954 (2003).

Tamai et al., "Transporter-mediated permeation of drugs across the blood-brain barrier," *J. Pharmaceutical Sciences*, 89(11):1371-1388 (2000).

Terasaki et al., "Conditionally immortalized cell lines as a new in vitro model for the study of barrier functions," *Biological and Pharmaceutical Bulletin*, 24(2):111-118 (2001).

A.

B.

| Competition | IC$_{50}$ (uM) | pIC$_{50}$ | SEM | % error |
|---|---|---|---|---|
| Phenylalanine | 160 | 3.8 | 0.1 | 2.5 |
| L-Dopa | 240 | 3.7 | 0.1 | 2.8 |
| Gabapentin | 400 | 3.4 | 0.09 | 2.6 |

A.

B.

| Exchange | Km (uM) | pKm | SEM | % error | Vmax (% GP) | SEM | % error |
|---|---|---|---|---|---|---|---|
| Phenylalanine | 98 | 4.0 | 0.07 | 1.7 | 45 | 1.9 | 4.2 |
| L-Dopa | 230 | 3.7 | 0.17 | 4.5 | 62 | 12 | 20 |
| Gabapentin | 640 | 3.2 | 0.07 | 2.1 | 100 | | |

Figure 12
A.
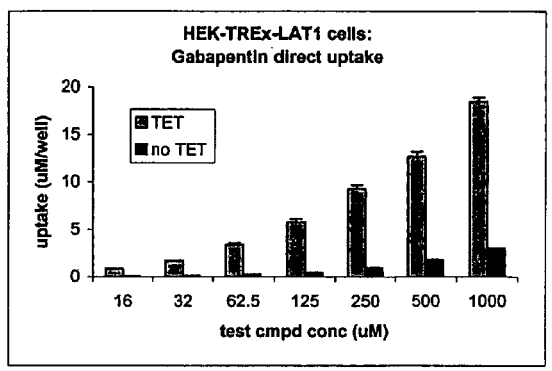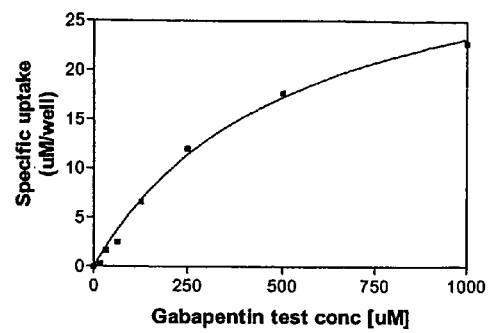
B.
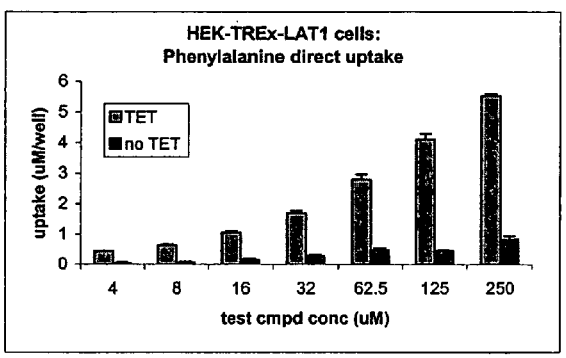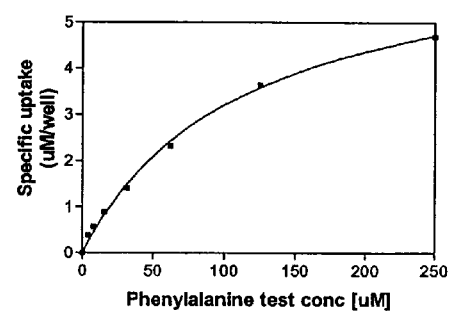
C.
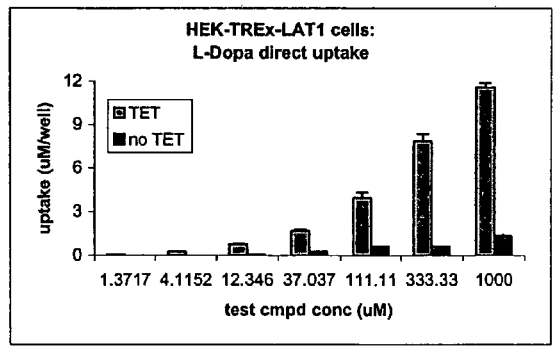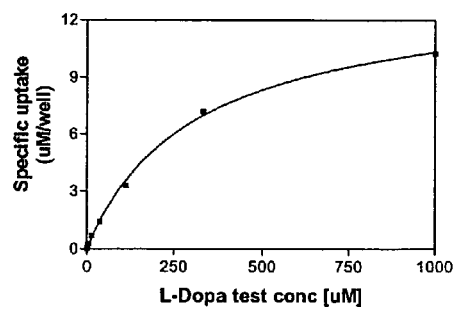

Figure 12. (cont.)
D.
| Direct Uptake | Km (uM) | pKm | SEM | % error | Vmax (pmol/sec/well) | SEM | % error |
|---|---|---|---|---|---|---|---|
| Phenylalanine | 140 | 3.9 | 0.05 | 1.3 | 3.2 | 0.22 | 6.9 |
| L-Dopa | 230 | 3.7 | 0.09 | 2.4 | 5.1 | 0.37 | 7.2 |
| Gabapentin | 500 | 3.3 | 0.05 | 1.6 | 6.7 | 1.3 | 19 |
Figure 13.
α-methyl dopa
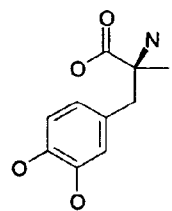
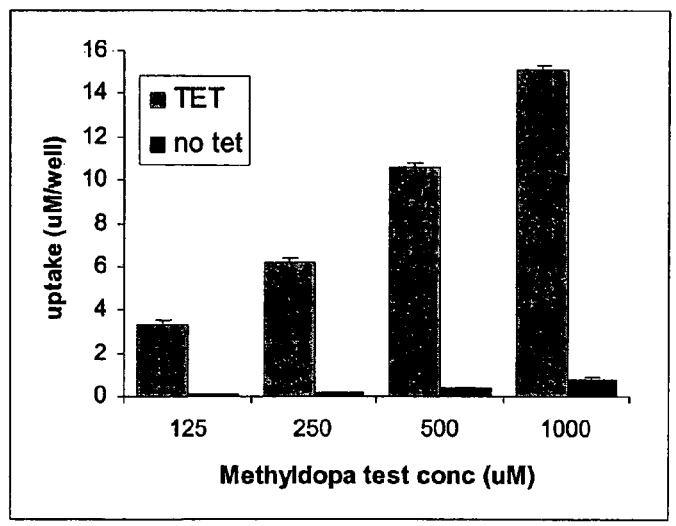

LAT1 TRANSPORTERS EXPRESSED IN BLOOD BRAIN BARRIER CELLS

CONTINUITY

This application claims the benefit of U.S. Provisional Application No. 60/540,754, filed Jan. 30, 2004, the disclosure of which is incorporated by reference herein in its entirety.

TECHNICAL FIELD

The disclosures herein relate to assays and methods of using the same for screening compounds and/or chemical moieties for their ability to be actively transported across the blood brain barrier.

BACKGROUND

The capillaries that supply blood to the tissues of the brain constitute the blood brain barrier (Goldstein et al. (1986) Scientific American 255:74-83; Pardridge, W. M. (1986) Endocrin. Rev. 7:314-330). The endothelial cells which form the brain capillaries are different from those found in other tissues in the body. Brain capillary endothelial cells are joined together by tight intercellular junctions which form a continuous wall against the passive diffusion of molecules from the blood to the brain and other parts of the central nervous system (CNS). These cells are also different in that they have few pinocytic vesicles which in other tissues allow somewhat unselective transport across the capillary wall. Also lacking are continuous gaps or channels running between the cells which would allow unrestricted passage.

The blood-brain barrier functions to ensure that the environment of the brain is constantly controlled. The levels of various substances in the blood, such as hormones, amino acids and ions, undergo frequent small fluctuations which can be brought about by activities such as eating and exercise (Goldstein et al., cited supra). If the brain was not protected by the blood brain barrier from these variations in serum composition, the result could be uncontrolled neural activity.

The isolation of the brain from the bloodstream is not complete. If this were the case, the brain would be unable to function properly due to a lack of nutrients and because of the need to exchange chemicals with the rest of the body. The presence of specific transport systems within the capillary endothelial cells assures that the brain receives, in a controlled manner, all of the compounds required for normal growth and function. In many instances, these transport systems consist of membrane-associated proteins which selectively bind and certain molecules across the barrier membranes. These transporter proteins are known as solute carrier transporters.

The problem posed by the blood-brain barrier is that, in the process of protecting the brain, it excludes many potentially useful therapeutic agents. Presently, only substances which are sufficiently lipophilic can penetrate the blood-brain barrier (Goldstein et al., cited supra; Pardridge, W. M., cited supra). Some drugs can be modified to make them more lipophilic and thereby increase their ability to cross the blood brain barrier. However, each modification must be tested individually on each drug and the modification can alter the activity of the drug.

Because the blood brain barrier is composed of brain microvessel endothelial cells, these cells have been isolated and cultured for use in in vitro model systems for studying the blood brain barrier (Bowman et. al, Brain microvessel endothelial cells in tissue culture: A model for study of blood-brain barrier permeability, Ann. Neurol. 14, 396-402 (1983); Audus and Borchardt, Characterization of an in vitro blood-brain barrier model system for studying drug transport and metabolism, Pharm. Res. 3, 81-87 (1986)). In vitro model systems of the blood brain barrier have been successfully derived from bovine, canine, human, murine, porcine, and rat cells, and have similar permeability properties due to similarity of the physiological characteristics of the blood brain barrier among mammals (Cserr et al., Blood-brain interfaces in vertebrates: a comparative approach, Am. J. Physiol. 246, R277-R288 (1984); Audus et al., The use of cultured epithelial and endothelial cells for drug transport and metabolism studies, Pharm. Res. 7, 435-451 (1990)). In these models, the cultured endothelial cells retain the characteristics of brain endothelial cells in vivo, such as morphology, specific blood brain barrier enzyme markers, and tight intercellular junctions. The cells can also be used for the study of passive diffusion, carrier mediated transport, and metabolism to specific factors affecting the blood brain barrier permeability. However, passaging of brain microvessel endothelial cells results in loss of specific endothelial and blood brain barrier markers as well as tight intercellular junctions (Brightman and Neuwelt (ed.), Implications of the blood-brain barrier and its manipulation, Vol. 1, Plenum Medical, New York, pp. 53-83 (1989)).

Currently, primary cultures of brain microvessel endothelial cells are the principal tool for in vitro prediction of blood brain barrier permeability. Isolated and cultured primary brain cells developed previously have exhibited different properties primarily due to considerable variability in the starting material. For example, with respect to transcellular transport, rigorous comparison of data between different laboratories has been very difficult (Pardridge et al., Comparison of in vitro and in vivo models of drug transcytosis through the blood-brain barrier, J. Pharmacol. Exp. Thera. 253, 884-891 (1990); Masereeuw et al., In vitro and in vivo transport of zidovudine (AZT) across the blood-brain barrier and the effect of transport inhibitors. Pharm. Res., 11, 324-330 (1994)). Passaging primary cells can affect the differentiation of cells and lead to the selection of the most rapidly proliferating clones. Furthermore, the expression of some marker enzymes such as gamma-glutamyl transpeptidase as well as tight junctional complexity has been shown to decrease with time in culture and passage number (Meresse et. al., Bovine brain endothelial cells express tight junctions and monoamine oxidase activity in long-term culture, J. Neuorchem. 53, 1363-1371 (1989)). Some transporter substrates have been demonstrated to accumulate in the brain (see U.S. Pat. No. 6,489,302).

Thus, it is apparent that the presently available clones of immortalized brain microvessel endothelial cell cultures suffer from individual drawbacks in terms of phenotype expression and homogeneic maintenance of that expression. This leads to difficulties with respect to accuracy and reproducibility in studies utilizing brain microvessel endothelial cells to model passage of chemical compounds and moieties, e.g., potential therapeutic compounds and/or drug moieties, across the blood brain barrier.

SUMMARY

Disclosed herein are methods of screening agents, conjugates or conjugate moieties for the ability to enter the CNS by crossing the blood brain barrier in order to treat or diagnose conditions within the CNS. These methods entail providing a cell expressing an LAT1 transporter, the transporter being situated in the plasma membrane of the cell. The cell is contacted with an agent, conjugate or conjugate moiety. Whether the agent, conjugate or conjugate moiety passes through the plasma membrane via the LAT1 transporter is determined. If the method comprises contacting the cell with an agent, the agent is a neuropharmaceutical agent or an imaging component. If the method comprises contacting the cell with a conjugate, the conjugate comprises an agent that is a neuropharmaceutical agent or an imaging component. If the method comprises contacting the cells with a conjugate moiety, the method further comprises linking the conjugate moiety to an agent that is a neuropharmaceutical agent or an imaging component. In some methods, the agent is other than a chemotherapeutic agent, an imaging agent or other agent used for treating or diagnosing cancer.

In some methods, if the agent is a cytotoxic agent or an imaging component, the method further comprises administering the agent, conjugate, or conjugate moiety to a peripheral tissue of an animal and measuring the amount of agent, conjugate, or conjugate moiety that passes through the blood brain barrier into the brain of the animal. In other methods, if the agent is a cytotoxic agent or an imaging component, the method further comprises contacting the agent to one side of a polarized monolayer of brain microvessel endothelial cells; and determining whether the agent is transported across the polarized monolayer.

In some methods, the cell endogenously expresses a LAT1 transporter. In other methods a nucleic acid molecule encoding a LAT1 transporter has been transfected or injected into the cell. In some methods the cell is a brain microvessel endothelial cell. In other methods the cell is an oocyte. In other methods the cell is a human embryonic kidney (HEK) cell. In other methods the cell is a Madin Darby canine kidney cell (MDCK). In still other methods, the cell is constructed to conditionally express the transporter.

In some methods the agent, conjugate or conjugate moiety comprises an L-amino acids with bulky (>2 atoms), uncharged, and hydrophobic or aromatic side-chains; a similarly structured D-amino acid; or a gamma amino acid such as gabapentin; or a cyclic alpha amino acid such as bicyclohexane amino acid. In some methods the agent, conjugate or conjugate moiety is administered to an undiseased animal and any toxic effects are determined. In some methods the neuropharmaceutical agent is a cytotoxic neuropharmaceutical agent selected from the group consisting of platinum, nitrosourea, a phosphoramide group that is selectively cytotoxic to brain tumor cells, nitroimidizole, and nitrogen mustard.

Disclosed herein are methods of screening agents, conjugates or conjugate moieties for the ability to enter the CNS by crossing the blood brain barrier wherein a cell used for testing is a brain microvessel endothelial cell that is one of a plurality of brain microvessel endothelial cells forming a polarized monolayer. An agent, conjugate or conjugate moiety is contacted to one side of the polarized monolayer and whether the agent, conjugate or conjugate moiety is transported into the brain microvessel endothelial cells or to the opposite side of the polarized monolayer is determined. Some methods further comprise administering the agent, conjugate, or conjugate moiety to a peripheral tissue of an animal and measuring the amount of agent, conjugate, or conjugate moiety that passes through the blood brain barrier into the brain of the animal.

Disclosed herein are methods of screening an agent, conjugate or conjugate moiety for neuropharmacological activity useful for treating neurological disorders. In these methods, one determines whether the agent, conjugate or conjugate moiety is transported through a LAT1 transporter. One then administers the agent, conjugate or conjugate moiety to a test animal and determines whether the agent, conjugate or conjugate moiety is actively transported across the blood brain barrier by measuring agent, conjugate or conjugate moiety concentrations found in the CNS of the animal. For those agents, conjugates or conjugate moieties that are transported in sufficient quantities, the agents, conjugates or conjugate moieties can be further tested in animals suffering from a particular neurological disorder to determine whether the agents, conjugates or conjugate moieties have the requisite therapeutic neuropharmacological activity for treating such neurological disorder.

Also disclosed herein are methods for in vitro screening of agents, conjugates or conjugate moieties for improved retention in the CNS. In these methods, one determines the substrate properties of a compound on both uptake transporters and efflux transporters. An agent, conjugate or conjugate moiety is first tested for activity on the LAT1 transporter. The agent, conjugate or conjugate moiety is then tested for substrate activity on an efflux transporter, such as P Glycoprotein (PgP). Those agents, conjugates or conjugate moieties active on both the efflux transporter and LAT1 are then modified and tested for a reduction of efflux substrate activity and retested for retention of activity on the LAT1 transporter. This iterative process produces an agent, conjugate or conjugate moiety with an increased ratio of substrate activities in the uptake and efflux systems, and improved retention of pharmacological levels of the modified agent, conjugate or conjugate moiety in the CNS.

Disclosed herein are methods of screening an agent, conjugate or conjugate moiety for capacity to be transported into the brain, comprising determining whether the agent, conjugate or conjugate moiety specifically binds to a LAT1 transporter, contacting the agent to one side of a polarized monolayer of cells, and determining whether the agent is actively transported across the polarized monolayer. In some methods the specific binding is determined by contacting a cell expressing the LAT1 transporter, the transporter being situated in the plasma membrane of the cell, with a substrate of the LAT1 transporter, and determining whether the agent inhibits transport of the substrate across the polarized monolayer.

Disclosed herein are pharmaceutical compositions comprising a therapeutic neuropharmaceutical agent, a cytotoxic neuropharmaceutical agent or an imaging component linked to a conjugate moiety to form a conjugate in which the conjugate moiety has a higher $V_{max}$ for the LAT1 transporter than the therapeutic neuropharmaceutical agent, cytotoxic neuropharmaceutical agent or imaging component alone. Some pharmaceutical compositions have at least 5 times the $V_{max}$ for LAT1 than the neuropharmaceutical agent or the imaging component alone. In some pharmaceutical compositions the conjugate has a $V_{max}$ for LAT1 that is at least 5% of the $V_{max}$ for LAT1 of a compound selected from the group comprising tryptophan, leucine, methionine, phenylalanine, bicyclohexane amino acid, L-dopa, gabapentin, and baclofen. In some pharmaceutical compositions the conjugate has a lower $V_{max}$ for an efflux transporter than the neuropharmaceutical agent or the imaging component alone. In some pharmaceutical compositions, the agent is not a cytotoxic agent, an imaging agent or other agent used for treating or diagnosing cancer.

Disclosed herein are methods of formulating a therapeutic neuropharmaceutical agent, a cytotoxic neuropharmaceutical agent or an imaging component. These methods entail linking the therapeutic neuropharmaceutical agent, the cytotoxic neuropharmaceutical agent or the imaging component to a conjugate moiety to form a conjugate, wherein the conjugate moiety has a greater $V_{max}$ for a LAT1 transporter than the component alone. The conjugate is formulated with a pharmaceutical carrier as a pharmaceutical composition. In some methods, the agent is not a cytotoxic agent, an imaging agent or other agent used for treating or diagnosing cancer.

Disclosed herein are methods of delivering a therapeutic neuropharmaceutical agent, a cytotoxic neuropharmaceutical agent or an imaging component. The methods involve administering to a patient a pharmaceutical composition comprising a therapeutic neuropharmaceutical agent, a cytotoxic neuropharmaceutical agent or an imaging component linked to a conjugate moiety to form a conjugate, wherein the conjugate has a higher $V_{max}$ for a LAT1 transporter than the therapeutic neuropharmaceutical agent, cytotoxic neuropharmaceutical agent or imaging component alone, whereby the conjugate passes through brain microvessel endothelial cells which make up the blood brain barrier, via the LAT1 transporter, into the CNS of the patient. Also disclosed herein are methods of delivering a conjugate, comprising administering to a patient a pharmaceutical composition comprising a neuropharmaceutical agent or imaging component linked to a conjugate moiety to form the conjugate, wherein the conjugate has a higher $V_{max}$ for a LAT1 transporter than the neuropharmaceutical agent or imaging component alone. In some methods the $V_{max}$ of the conjugate is at least two-fold higher than that of the neuropharmaceutical agent or imaging component alone. In some methods the neuropharmaceutical agent is a cytotoxic neuropharmaceutical selected from the group consisting of platinum, nitrosourea, a phosphoramide group selectively cytotoxic to brain tumor cells, nitroimidizole, and nitrogen mustard. In some methods, the agent is not a cytotoxic agent, an imaging agent or other agent used for treating or diagnosing cancer.

Disclosed herein are methods of treating neurological disorders. These methods entail administering to a patient an effective amount of an agent that is transported by LAT1, wherein the agent is a conjugate comprising a therapeutic neuropharmaceutical agent, a cytotoxic neuropharmaceutical agent or an imaging component linked to a conjugate moiety.

Disclosed herein are methods of screening an agent for decreased side effects in the central nervous system (CNS), comprising providing an agent having a pharmacological activity, wherein the pharmacological activity is useful for treating a disease present in a tissue other than the CNS, and the pharmacological activity results in undesired side effects in the CNS if the agent enters the CNS, modifying the agent, providing a cell expressing at least one efflux transporter protein that transports substrates out of the CNS, contacting the cell with the modified agent, and determining whether the modified agent is transported by the at least one efflux transporter protein with a higher $V_{max}$ than the agent, a higher $V_{max}$ indicating that the modification increases the capacity of the modified agent relative to the agent to be transported out of the CNS, thereby decreasing undesired side effects in the CNS.

BRIEF DESCRIPTION OF THE DRAWINGS

FIG. 12 shows direct uptake assays using HEK-TREx-LAT1-4F2hc cells with gabepentin, phenylalanine and L-Dopa as substrates. (A) Dose-response (left) and specific uptake (right) of gabapentin into cells induced (+ TET) or uninduced (no TET) to express hLAT1. (B) Dose-response (left) and specific uptake (right) of phenylalanine into cells induced (+ TET) or uninduced (no TET) to express hLAT1. (C) Dose-response (left) and specific uptake (right) of L-Dopa into cells induced (+ TET) or uninduced (no TET) to express hLAT1. Specific uptake was determined by subtracting the values obtained in cells not induced to express hLAT1 from those in the induced cells and graphed vs. the test concentration of each substrate. (D) A summary of the results in each assay including the assay variability (% error).

FIG. 13 shows uptake of different concentrations of α-methyl-Dopa into HEK-TREx-LAT1-4F2hc cells induced (+ TET) or uninduced (no TET) to express hLAT1.

DEFINITIONS

Figure 1:
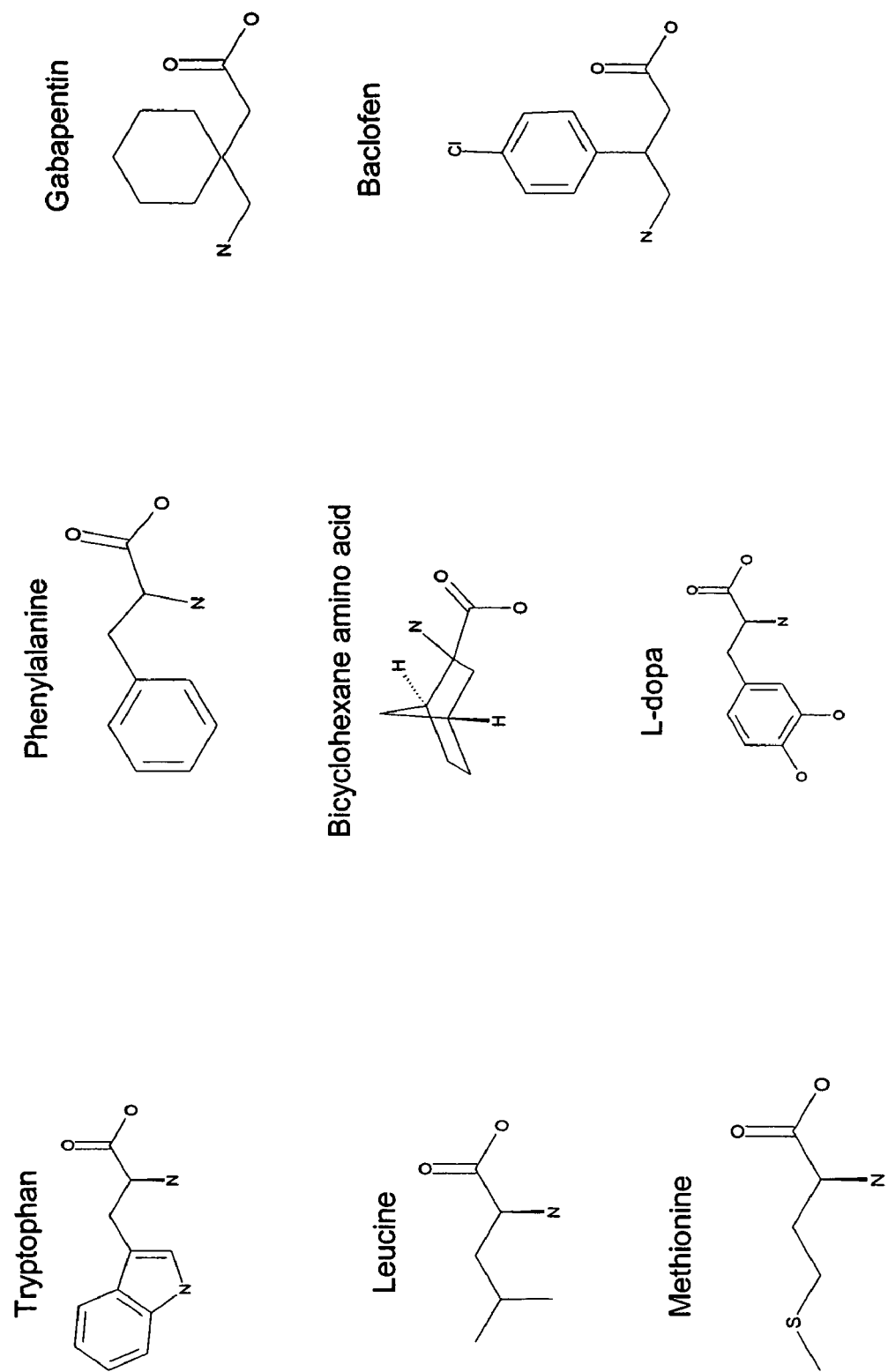
FIG. 1 shows the structures of known substrates of the LAT1 transporter.

"Transport by passive diffusion" refers to transport of an agent that is not mediated by a specific transporter protein. An agent that is substantially incapable of passive diffusion has a permeability across a standard cell monolayer (e.g., Caco-2 or MDCK cells or an artificial bilayer (PAMPA)) of less than $5 \times 10^{-6}$ cm/sec, and usually less than $1 \times 10^{-6}$ cm/sec in the absence of an efflux mechanism.

A "substrate" of a transporter protein is a compound whose uptake into or passage through the plasma membrane of a cell is facilitated at least in part by a transporter protein.

The term "ligand" of a transporter protein includes compounds that bind to the transporter protein. Some ligands are transported and are thereby also substrates. Some ligands inhibit or antagonize transport of a substrate by the transporter protein. Some ligands bind in a manner non-competitive with substrates and modulate the transport of substrates by the transporter protein.

The term "neuropharmaceutical agent" is used to describe a compound that has or may have a pharmacological activity in the treatment or prophylaxis of a neurological disorder. Neuropharmaceutical agents include compounds that are known drugs, compounds for which pharmacological activity has been identified but which are undergoing further therapeutic evaluation, and compounds that are members of collections and libraries that are to be screened for a pharmacological activity. The neuropharmaceutical agent can be a compound having a therapeutic, prophylactic or cytotoxic effect on a neurological disease including any condition which affects biological functioning of the central nervous system. Examples of neurological diseases include cancer (e.g., brain tumors), Acquired Immune Deficiency Syndrome (AIDS), stroke, epilepsy, Parkinson's disease, multiple sclerosis, neurodegenerative disease, trauma, depression, Alzheimer's disease, migraine, pain, or a seizure disorder. Classes of neuropharmaceutical agents include proteins, antibiotics, adrenergic agents, anticonvulsants, small molecules, nucleotide analogs, chemotherapeutic agents, anti-trauma agents, peptides and other classes of agents used in treatment or prophylaxis of a neurological disorder. Examples of proteins include CD4 (including soluble portions thereof), growth factors (e.g., nerve growth factor and interferon), dopamine decarboxylase and tricosanthin. Examples of antibiotics include amphotericin B, gentamycin sulfate, and pyrimethamine. Examples of adrenergic agents (including blockers) include dopamine and atenolol. Examples of chemotherapeutic agents include adriamycin, methotrexate, cyclophosphamide, etoposide, and carboplatin. An example of an anticonvulsant which can be used is valproate and an anti-trauma agent which can be used is superoxide dismutase. Examples of peptides are somatostatin analogues and enkephalinase inhibitors. Nucleotide analogs which can be used include azido thymidine (hereinafter AZT), dideoxy Inosine (ddI) and dideoxy cytodine (ddc).

The term "agent" is used to describe a compound that has or may have a pharmacological activity. Agents include compounds that are known drugs, compounds for which pharmacological activity has been identified but which are undergoing further therapeutic evaluation, and compounds that are members of collections and libraries that are to be screened for a pharmacological activity.

A "pharmacological" activity means that an agent exhibits an activity in a screening system that indicates that the agent is or may be useful in the prophylaxis or treatment of a disease. The screening system can be in vitro, cellular, animal or human. Agents can be described as having pharmacological activity notwithstanding that further testing may be required to establish actual prophylactic or therapeutic utility in treatment of a disease.

An agent is "orally active" if it can exert a pharmacological activity when administered via an oral route.

A "peripheral tissue" means a tissue other than the CNS.

A "conjugate" refers to a compound comprising a neuropharmaceutical agent or imaging component and a chemical moiety bound thereto, which moiety by itself or in combination with the neuropharmaceutical agent or imaging component renders the conjugate a substrate for active transport, for example rendering the conjugate to be a substrate for a transporter protein. The chemical moiety may or may not be subject to cleavage from the neuropharmaceutical agent or imaging component upon uptake and metabolism of the conjugate in the patient's body. In other words, the moiety may be cleavably bound to the neuropharmaceutical agent or imaging component or non-cleavably bound to the neuropharmaceutical agent or imaging component. The bond can be a direct (i.e., covalent) bond or the bond can be through a linker. In cases where the bond/linker is cleavable by metabolic processes, the neuropharmaceutical agent or imaging component, or a further metabolite of the neuropharmaceutical agent or imaging component, is the therapeutic or imaging entity. In cases where the bond/linker is not cleavable by metabolic processes, the conjugate itself is the therapeutic or imaging entity. Most typically, the conjugate comprises a prodrug having a metabolically cleavable moiety, where the conjugate itself does not have pharmacological activity but the component to which the moiety is cleavably bound does have pharmacological activity. Typically, the moiety facilitates therapeutic use of the neuropharmaceutical agent or imaging component by promoting uptake of the conjugate via a transporter. Thus, for example, a conjugate comprising a neuropharmaceutical agent and a conjugate moiety may have a $V_{max}$ for a transporter that is at least 2, 5, 10, 20, 50 or 100-fold higher than that of the neuropharmaceutical agent or imaging component alone. A conjugate moiety can itself be a substrate for a transporter or can become a substrate when linked to the neuropharmaceutical agent or imaging component. Examples of preferred conjugate moieties are tryptophan, leucine, methionine, phenylalanine, Bicyclohexane amino acid, L-dopa, gabapentin, and baclofen. Thus, a conjugate formed from a neuropharmaceutical agent or imaging component and a conjugate moiety can have higher CNS uptake activity than either the neuropharmaceutical agent, the imaging component, or the conjugate moiety alone.

A "neuropharmacological" activity means that a neuropharmaceutical agent exhibits an activity in a screening system that indicates that the neuropharmaceutical agent is or may be useful in the prophylaxis or treatment of a neurological disease. The screening system can be in vitro, cellular, animal or human. Neuropharmaceutical agents can be described as having neuropharmacological activity notwithstanding that further testing may be required to establish actual prophylactic or therapeutic utility in treatment of a disease.

$V_{max}$ and $K_m$ of a compound for a transporter are defined in accordance with convention. $V_{max}$ is the number of molecules of compound transported per second at saturating concentration of the compound. $K_m$ is the concentration of the compound at which the compound is transported at half of $V_{max}$. When the goal is to transport an agent, conjugate or conjugate moiety into the CNS, a high $V_{max}$ for an influx transporter such as LAT1 is generally desirable. Likewise for the same goal, a low value of $K_m$ is typically desirable for transport of a compound present at low blood concentrations. In some cases a high value of $K_m$ is acceptable for the transport of compounds present at high concentrations in the blood. For these reasons, the intrinsic capacity of a compound to be transported by a particular transporter is usually expressed as the ratio $V_{max}$ of the compound/$V_{max}$ of a reference compound known to be a substrate for the transporter. $V_{max}$ is affected both by the intrinsic turnover rate of a transporter (molecules/transporter protein) and transporter density in the plasma membrane, which depends on expression level. In certain instances, the goal is to avoid transport into the CNS. In these instances, low $V_{max}$ for all influx transporters and a high $V_{max}$ for all efflux transporters expressed in the blood brain barrier is desirable.

"EC50", or "effective concentration 50", is a measurement of the substrate concentration that results in a turnover rate 50% of the maximal turnover rate for the substrate (0.5 $V_{max}$).

A plasma membrane containing a monolayer of cells in physical contact with each other and having different sets of proteins embedded in the plasma membranes facing either side of the monolayer is described as being "polarized". For example, brain microvessel endothelial cells in the blood brain barrier have a luminal side facing capillaries and exposed to blood, and an abluminal side facing cells of the central nervous system and exposed to cerebrospinal fluid. The luminal plasma membrane contains a different set of transmembrane and membrane-associated components than the abluminal plasma membrane of the same cell. Brain microvessel endothelial cells in culture can also be polarized, where the cells form a monolayer in culture that has a luminal and abluminal side. MDCK cells, when grown on filter membranes in transwell dishes, form a polarized monolayer in which one side of the monolayer is the apical side and the other is the basolateral side.

"Sustained release" refers to release of a therapeutic or prophylactic amount of a drug or an active metabolite thereof over a period of time that is longer than a conventional formulation of the drug. For oral formulations, the term "sustained release" typically means release of the drug within the GI tract lumen over a period of from about 2 to about 30 hours, more typically over a period of about 4 to about 24 hours. Sustained release formulations achieve therapeutically effective concentrations of the drug in the systemic blood circulation over a prolonged period of time relative to that achieved by oral administration of a conventional formulation of the drug. "Delayed release" refers to release of the drug or an active metabolite thereof into the gastrointestinal lumen after a delay time period, typically a delay of about 1 to about 12 hours, relative to that achieved by oral administration of a conventional formulation of the drug.

The phrase "specifically binds" when referring to a substrate or ligand of a LAT1 transporter refers to a specific interaction between a substrate or ligand and the LAT1 transporter in which the substrate or ligand binds preferentially with a LAT1 transporter and does not bind in a significant amount to most or any other proteins present in a biological sample. A substrate or ligand that specifically binds to a LAT1 transporter often has an association constant of $10\text{-}10^3$ M$^{-1}$, $10^5$ M$^{-1}$, $10^6$ M$^{-1}$ or $10^7$ M$^{-1}$, preferably $10^8$ M$^{-1}$ to $10^9$ M$^{-1}$ or higher. However, some substrates or ligands of LAT1 transporters have much lower affinities and yet the binding can still be shown to be specific. Substrates of LAT1 can specifically bind to LAT1 and other proteins such as efflux transporters without specifically binding to other proteins.

"$P_{app}$", or "apparent permeability", is a value that reflects the permeability of a test compound through a cell layer such as a polarized monolayer. The equation for determining $P_{app}$ is as follows:

$$P_{app} = \frac{V \cdot dC}{A \cdot C_0 \cdot dt} \text{(cm/sec)}$$

where,
V=volume of receiving chamber (in cm$^3$, i.e., ml);
dC/dt=steady state rate of appearance of applied compound in receiving chamber after primary lag time (in μM/sec);
$C_0$=concentration of compound in the donor chamber (in μM)
A=area of the cell layer (in cm$^2$)

"Allelic variants" at the DNA level are the result of genetic variation between individuals of the same species. Some allelic variants at the DNA level that cause substitution, deletion or insertion of amino acids in proteins encoded by the DNA result in corresponding allelic variation at the protein level.

"Cognate forms" of a gene refers to variation between structurally and functionally related genes between species. For example, the human gene showing the greatest sequence identity and closest functional relationship to a mouse gene is the human cognate form of the mouse gene.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

Another example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information web site. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. For identifying whether a nucleic acid or polypeptide is within the scope hereof, the default parameters of the BLAST programs are suitable. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix. The TBLASTN program (using protein sequence for nucleotide sequence) uses as defaults a word length (W) of 3, an expectation (E) of 10, and a BLOSUM 62 scoring matrix. (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance.

For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

DETAILED DESCRIPTION

I. General

LAT1 is shown herein to be expressed at high levels in brain microvessel endothelial cells. This finding can be used to generate or isolate conjugates and agents having neuropharmacological or imaging activity useful for treatment, prophylaxis or diagnosis of neurological diseases. The invention provides methods of identifying agents, conjugates or conjugate moieties that are substrates for LAT1. For therapeutic purposes, agents or conjugates having inherent neuropharmacologic activity can be screened to determine whether they are substrates for LAT1. Alternatively, a conjugate moiety lacking such activity can be screened, and linked to a neuropharmacologic agent after screening. Agents or conjugates that both have neuropharmacologic activity and are substrates for LAT1 are preferentially transported into the CNS via LAT1 transporters after administration to a patient. Such an agent or conjugate by itself or in combination with another agent is effective in treatment or prophylaxis of a neurological disease. An analogous approach is used for imaging features of the brain. Agents and conjugates that have an imaging component and are substrates for LAT1 are preferentially transported into the CNS via LAT1 transporters. The imaging component is then detected by various methods such as detecting radioactive decay of the imaging component. The agents and conjugates can be used to image brain tumors overexpressing the LAT1 transporter. Optionally, the agents or conjugates have inherent affinity for, or are provided with a conjugate moiety that confers affinity for, a particular antigen or cell type within the brain. For example, the agents or conjugates can be provided with a targeting moiety to Aβ to allow imaging of plaques in Alzheimer's patients.

II. LAT1 transporter

The family of amino acid transporter/permeases (AAPs) contains at least 13 members in humans (SLC7A1-13). AAP transporters have 12 putative transmembrane domains, with both the amino and carboxy termini located on the cytoplasmic side. A sub-family of AAPs (referred to as LAT1 and LAT2) is specialized for the transport of large aromatic neutral amino acids. LAT1 and LAT2 transport a variety of neutral amino acids (leucine, valine, isoleucine, phenylalanine, tryptophan and methionine) and amino acid analogs (L-dopa, gabapentin, and bicyclohexane amino acid (BCH)). Both LAT1 and LAT2 co-assemble with the glycoprotein 4F2HC. LAT1 and LAT2 transporters are obligate exchange transporters. Thus, for each amino acid transported across the plasma membrane into the cell, another amino acid is effluxed out of the cell.

It is now shown that LAT1 is highly expressed in brain microvessel endothelial cells. LAT1 is expressed at a level nearly 10-fold higher than other LAT family transporters with similar substrate specificity. It is desirable to generate agents, conjugates, and conjugate moieties for transport into the CNS that have activity for LAT1 due to this high expression level. The GenBank accession number for human LAT1 is NM_003983 (SEQ ID NO:1). The GenBank accession number for human 4F2HC is AB018010 (SEQ ID NO:2). Unless otherwise apparent from the context, reference to a transporter includes the amino acid sequence described in or encoded by the GenBank reference numbers NM-003983 and AB018010, and, allelic, cognate and induced variants and fragments thereof retaining essentially the same transporter activity. Usually such variants show at least 90% sequence identity to the exemplary Genbank nucleic acid or amino acid sequence.

III. Methods of Screening to Identify LAT1 Substrates

Agents known or suspected to have a neuropharmaceutical activity or to comprise an imaging component can be screened directly for their capacity to act as substrates of LAT1. Alternatively, conjugate moieties can be screened as substrates, and the conjugate moieties are then linked to a neuropharmaceutical agent or imaging component. In such methods, the conjugate moieties can optionally be linked to a neuropharmaceutical agent or imaging component, or other molecule during the screening process. If another molecule is used in place of a neuropharmaceutical agent or imaging component, the molecule can be chosen to resemble the structure of a neuropharmaceutical agent or imaging component ultimately intended to be linked to the conjugate moiety for neuropharmaceutical use. Alternatively, a conjugate moiety can be screened for a substrate activity alone and linked to a neuropharmaceutical agent or imaging component after screening.

LAT1 proteins preferably transport L-amino acids with bulky (>2 atoms), uncharged and hydrophobic or aromatic side-chains. LAT1 also transports similar D-amino acids with lower affinity than L-amino acids. Additionally, LAT1 transports several gamma amino acids such as gabapentin and cyclic alpha amino acids such as bicyclohexane amino acid. The structures of each compound listed in Table 1 are depicted in FIG. 1.

TABLE 1

| SUBSTRATES | Reported Affinity for LAT1 |
|---|---|
| Tryptophan | 0.35 mM |
| Leucine | 0.22 mM |
| Methionine | 0.25 mM |
| Phenylalanine | 0.025 mM |
| Bicyclohexane amino acid | 0.18 mM |
| L-dopa | 0.05 mM |
| Gabapentin | 0.15 mM |
| Baclofen | 0.25 mM |

Tryptophan, leucine, methionine, phenylalanine, bicyclohexane amino acid, L-dopa, α-methyl dopa, gabapentin, and baclofen are examples of LAT1 substrates that are candidates for conjugation to therapeutic neuropharmaceutical agents, cytotoxic neuropharmaceutical agents and imaging components.

In some screening methods, the cells are transfected with DNA encoding the LAT1 transporter. HEK (human embryonic kidney) and CHO (Chinese hamster ovary) cells, for example, are suitable for transfection. Oocytes can be injected with LAT1 cRNA to express LAT1 transporter. In some methods, the only transporter expressed by the cells is the LAT1 transporter. In other methods, cells express LAT1 in combination with other transporters. In still other methods, agents, conjugate moieties or conjugates are screened on different cells expressing different transporters. Agents, conjugate moieties or conjugates can be screened either for specificity for the LAT1 transporter or for transport into cells endogenously expressing a plurality of transporters. In some methods, the results of a screening method (e.g., a competition uptake, exchange or direct uptake assay) using a cell expressing the LAT1 transporter can be compared with the results of a control cell(s) lacking the LAT1 transporter or in the presence of a specific inhibitor of the LAT1 transporter.

In some methods, cells endogenously expressing the LAT1 transporter are used. Brain microvessel endothelial cells, for example, endogenously express the LAT1 transporter, as demonstrated in Example 1. Agents, conjugate moieties or conjugates can be screened for transport into cultured brain microvessel endothelial cells. Passaging cultures of brain microvessel endothelial cells typically causes the cells to lose differentiation characteristics such as the ability to form tight junctions. The propensity of passaged cells to lose differentiation characteristics can be avoided through the use of brain microvessel endothelial cells that are transformed with an SV40 large T antigen. See Terasaki et al., Drug Discovery Today 8:944-954 (2003). Inducible expression of the SV40 large T antigen allows cells to divide when the antigen is expressed and differentiate when the antigen is not expressed. Brain microvessel endothelial cells can be isolated from animals transgenic for the SV40 large T antigen, which can be expressed in a temperature-sensitive fashion. The cells are stimulated to divide by being cultured at the temperature at which the antigen is expressed. Once the cells have formed a monolayer, they are placed at a temperature at which the antigen is not expressed, causing the cells to stop dividing and differentiate. Differentiation results in the formation of tight junctions and the polarization of the plasma membranes. Monolayers of polarized cells are tested for the ability to transport agents, conjugates or conjugate moieties. In other methods, the ability to transport agents, conjugates or conjugate moieties is measured by administering the agent, conjugate, or conjugate moiety to a peripheral tissue of an animal. The amount of agent, conjugate, or conjugate moiety that passes through the blood brain barrier into the brain of the animal is measured either in the cerebral spinal fluid (CSF) or in whole brain tissue following brain perfusion with solution to remove compound from the brain vasculature. Generally, the brain penetration of the drug is reported as the ratio of the unbound compound in brain tissue or CSF to the unbound compound in the blood. In some methods, the measurement can be made on a specimen from the animal or in situ.

In some methods, the ability of an agent, conjugate or conjugate moiety to specifically bind to a LAT1 transporter is tested. A known substrate of the LAT1 transporter and the agent, conjugate or conjugate moiety are added to cells expressing the LAT1 transporter. The amount or rate of transport of the substrate in the presence of the agent, conjugate or conjugate moiety is compared to the amount or rate of transport of the agent, conjugate or conjugate moiety in the absence of the test compound. If the amount or rate of transport of the substrate is decreased by the presence of the agent, conjugate or conjugate moiety, the agent, conjugate or conjugate moiety binds the LAT1 transporter. Agents, conjugates or conjugate moieties that bind the LAT1 transporter can be further analyzed to determine if they are transported by the LAT1 transporter or only adhere to the exterior of the transporter. Agents, conjugates or conjugate moieties that are transported by the LAT1 transporter can be further tested to determine if they are transported from one side of a monolayer of polarized cells to the other side, such as a monolayer of brain microvessel endothelial cells. Agents and conjugates having neuropharmaceutical activity and that that are transported by the LAT1 transporter can be used to form pharmaceutical compositions. Conjugate moieties that are transported by the LAT1 transporter can be linked to a therapeutic or cytotoxic neuropharmaceutical agent or an imaging component.

Transport of a compound into a cell can be detected by detecting a signal from within a cell from any of a variety of reporters. The reporter can be as simple as a label such as a fluorophore, a chromophore, or a radioisotope. Confocal imaging can also be used to detect internalization of a label as it provides sufficient spatial resolution to distinguish between fluorescence on a cell surface and fluorescence within a cell; alternatively, confocal imaging can be used to track the movement of compounds over time. In another approach, transport of a compound is detected using a reporter that is a substrate for an enzyme expressed within a cell. Once the compound is transported into the cell, the substrate is metabolized by the enzyme and generates an optical signal that can be detected. Light emission can be monitored by commercial PMT-based instruments or by CCD-based imaging systems. In addition, assay methods utilizing liquid chromatography-mass spectroscopy (LC-MS-MS) detection of the transported compounds or electrophysiological signals indicative of transport activity are also employed. Mass spectroscopy is a powerful tool because it allows detection of very low concentrations of almost any compound, especially molecules for which a radiolabeled version is not available. It can also be used to distinguish substrates from nontransported ligands. These same detection methods can be used to determine if a compound is transported from one side of a monolayer of polarized cells to the other side by administering the compound to one side of the monolayer and sampling the media on the other side of the monolayer after a predetermined period of time.

In some methods, multiple agents, conjugates or conjugate moieties are screened simultaneously and the identity of each agent, conjugate or conjugate moiety is tracked using tags linked to the agents, conjugates or conjugate moieties. In some methods, a preliminary step is performed to determine binding of an agent, conjugate or conjugate moiety to a transporter. Although not all agents, conjugates or conjugate moieties that bind to a transporter are substrates of the transporter, observation of binding is an indication that allows one to reduce the number of candidates from an initial repertoire. In some methods, the transport rate of an agent, conjugate or conjugate moiety is tested in comparison with the transport rate of a reference substrate for that transporter. For example, gabapentin, a natural substrate of LAT1, can be used as a reference. The comparison can be performed in separate parallel assays in which an agent, conjugate or conjugate moiety under test and the reference substrate are compared for uptake on separate samples of the same cells. Alternatively, the comparison can be performed in a competition format in which an agent, conjugate or conjugate moiety under test and the reference substrate are applied to the same cells. Typically, the agent, conjugate or conjugate moiety and the reference substrate are differentially labeled in such assays.

In comparative assays, the $V_{max}$ of an agent, conjugate or conjugate moiety tested can be compared with that of a reference substrate. If an agent, conjugate moiety or conjugate has a $V_{max}$ of at least 1%, 5%, 10%, 20%, and most preferably at least 50% of the reference substrate for the LAT1 transporter, then the agent, conjugate moiety or conjugate is also a substrate for the LAT1 transporter. If transport of the agent, conjugate moiety or conjugate into the CNS is desired, a higher $V_{max}$ of the agent, conjugate moiety or conjugate relative to that of the reference substrate is preferred. Therefore, agents, conjugate moieties or conjugates having $V_{max}$'s of at least 1%, 5%, 10%, 20%, 50%, 100%, 150% or 200% (i.e., two-fold) of the $V_{max}$ of a reference substrate (e.g., gabapentin) for the transporter are screened in some methods. The components to which conjugate moieties are linked can by themselves show little or no detectable substrate activity for the transporter (e.g., $V_{max}$ relative to that of a reference substrate of less than 0.1% or 1%). Preferred agents, conjugates or conjugate moieties have a $V_{max}$ for LAT1 that is at least 5% of the $V_{max}$ for LAT1 of gabapentin. Preferred conjugates comprising a neuropharmaceutical agent or imaging component linked to a conjugate moiety preferably have a greater $V_{max}$ for LAT1 than the neuropharmaceutical agent or imaging component alone.

Having determined that an agent, conjugate or conjugate moiety is a substrate for LAT 1, a further screen can be performed to determine its therapeutic activity in treatment or prophylaxis of a disease, or its cytotoxic activity against brain tumor cells. Usually the disease is neurological (i.e., the pathology occurs in the CNS). Alternatively, the diseased tissue is non-CNS tissue but is responsive to treatment by an agent that exerts a pharmacological effect on the CNS that in turn causes an effect on the diseased non-CNS tissue, such as an effect caused by the release of hormones from the CNS. Diseases of this type are also considered to be diseases of the CNS unless otherwise apparent from context. If the agent, conjugate or conjugate moiety does not have inherent therapeutic or cytotoxic activity, it is first linked to another chemical component having such therapeutic or cytotoxic properties. The agent, conjugate or conjugate moiety is then contacted with cells expressing LAT1. The contacting can be performed either on a population of cells in vitro, or the brain microvessel endothelial cells of a test animal via administration of the agent, conjugate or conjugate moiety to a test animal. The therapeutic or cytotoxic activity of the agent, conjugate or conjugate moiety is then determined from established protocols for that particular disease. Optionally, the effect of the agent, conjugate or conjugate moiety can be compared with a placebo.

A further screen can be performed to determine toxicity of the agent, conjugate, or conjugate moiety to normal cells. The agent, conjugate or conjugate moiety is administered to a laboratory animal that is preferably in an undiseased state. Various tissues of the animal, such as liver, kidney, heart and brain are then examined for signs of pathology. Cells in the animal can also be analyzed for uptake of the agent, conjugate, or conjugate moiety.

IV. Iterative Modification and Testing of LAT1 Substrates

Having determined that an agent, conjugate or conjugate moiety is a substrate for LAT1, the agent, conjugate or conjugate moiety can be modified to improve its properties as a substrate. The modified agent, conjugate or conjugate moiety is then tested for transport by LAT1. Modified agents, conjugates or conjugate moieties that are transported by LAT1 at a higher $V_{max}$ compared to the unmodified agent, conjugate or conjugate moiety are preferred. The process of modifying agents, conjugates or conjugate moieties and testing for transport by LAT1 can be repeated until a desired level of transport is reached.

Agents, conjugates or conjugate moieties that are substrates of LAT1 can also be modified for decreased capacity to be transported out of cells by efflux transporters. An agent, conjugate or conjugate moiety transported by LAT1 is assayed to determine whether it is also a substrate for one or more efflux transporters. If the agent, conjugate or conjugate moiety is transported by an efflux transporter, the agent, conjugate or conjugate moiety is modified and tested for both reduced transport by an efflux transporter and retention of LAT1 substrate activity.

In some instances, the specific efflux transporter responsible for transporting an agent, conjugate or conjugate moiety is known. The agent, conjugate or conjugate moiety is modified, preferably by addition of a chemical group that differs in chemical characteristics from other known substrates of the efflux transporter. The modified agent, conjugate or conjugate moiety is then tested for retained capacity to be transported by LAT1 and a diminished capacity to be transported by an efflux transporter. It is not necessary that the modified agent, conjugate or conjugate moiety retain the same kinetic properties of LAT1 transporter substrate as the unmodified agent, conjugate or conjugate moiety as long as some LAT1 substrate activity is retained. Examples of efflux transporters are the P-glycoprotein (PgP), multidrug resistance protein (MRP1), and breast cancer resistance protein (BCRP). Preferred agents, conjugates or conjugate moieties have a LAT1 transport:efflux transport ratio of at least 1.1:1.0, more preferably, 2.0:1.0, and more preferably 5.0:1.0 and more preferably 10.0:1.0 or higher at a given concentration of agent, conjugate or conjugate moiety.

Efflux transporter activity can be measured in several ways. First, functional assays can be performed in which interaction of compounds with efflux transporters is measured by stimulation of efflux transporter ATPase activity in cellular membrane fragments or vesicles. Second, competition assays can be performed in which test compounds compete with known efflux substrates in whole cells. Third, direct transport assays can be performed in which the transport of compounds is measured across a polarized monolayer of cells. Other assays besides these three can also be used to directly or indirectly measure the efflux substrate characteristics of a test compound.

The efflux transporter ATPase assay is based on the fact that most efflux substrates increase the ATPase activity of efflux transporters upon binding. In one type of assay, Baculovirus membrane fragments or vesicles containing an efflux transporter such as PgP, as well as control membrane fragments or vesicles not containing the efflux transporter, are either prepared or obtained from commercial suppliers. The ATPase activity of the membrane fragments or vesicles is measured in the presence of various concentrations of the test compound. An agent, conjugate, or conjugate moiety that is transported by LAT1 is added to the ATPase assay reaction and the amount of ATPase activity is measured at various concentrations of agent, conjugate, or conjugate moiety. Parallel experiments are performed in which ATPase activity is measured under addition of the same concentrations of modified agent, conjugate, or conjugate moiety that retain LAT1 substrate activity. Reduced ATPase activity caused by the modified agent, conjugate, or conjugate moiety compared to the unmodified agent, conjugate, or conjugate moiety indicates that the modified agent, conjugate, or conjugate moiety is a better candidate for retention in the CNS.

In the competition assay, the test compound is assayed for competition with a known efflux substrate. For example, calcein-AM is a non-fluorescent compound that is a substrate of PgP and MRP1. Calcein-AM is initially loaded into the cells, for example, by transport by passive diffusion. Cells expressing these efflux transporters actively efflux nearly all of the calcein-AM that is present in the cells. However, when other efflux transporter substrates are present, these other substrates compete with calcein-AM for efflux, resulting in more calcein-AM accumulating inside the cells. Intracellular esterases convert the non-fluorescent calcein-AM to fluorescent calcein which can be measured spectrophotometrically. An agent, conjugate, or conjugate moiety that is transported by LAT1 is loaded into efflux transporter-containing cells by either LAT1 transport or passive diffusion. Calcein-AM is also loaded into the cells by active transport or transport by passive diffusion. Accumulation of calcein-AM is measured and compared to the amount of accumulation in the absence of the agent, conjugate, or conjugate moiety. Parallel experiments are performed in which a modified agent, conjugate, or conjugate moiety that is (transported by LAT1 is loaded into the cells. Accumulation of calcein-AM is measured and compared to the amount of accumulation in the absence of the modified agent, conjugate, or conjugate moiety. Decreased calcein-AM accumulation inside the cells caused by the presence of a unmodified agent, conjugate, or conjugate moiety compared to calcein-AM accumulation in the presence of unmodified agent, conjugate, or conjugate moiety indicates that the modified agent, conjugate, or conjugate moiety is a better candidate for retention inside the CNS.

The cells used for competition assays can be cells that either express a high endogenous level of the efflux transporter of interest or are transformed with an expression vector containing the efflux transporter gene. Suitable cell lines for efflux assays are, for example, HEK and MDCK cell lines into which the PgP gene has been transfected, or MES-SA/Dx5 uterine sarcoma cells grown in the presence of 500 nM doxorubicin, which express a high endogenous level of PgP. These cells can optionally be transfected with the LAT1 transporter gene. Preferred cells express both one or more efflux transporter genes such as PgP and the LAT1 gene, either endogenously or through transfection of expression vectors.

A third type of efflux transporter assay is the cellular transwell monolayer efflux assay. In this assay, cells expressing efflux transporters, such as MDCK cells containing the TREx-PgP expression vector, are seeded and grown in transwell dishes on filter membranes made of substances such as polycarbonate. The cells form a polarized monolayer. The transwell dishes have apical and basolateral chambers that are separated by the filter membrane on which the polarized monolayer is situated. Assays are performed by placing a test compound in either the apical or basolateral chamber, followed by sampling the opposite chamber after a predetermined period of time such as 60-120 minutes and measuring the amount of the test compound. The test compound can be measured by methods such as radiolabel detection or LC-MS-MS analysis. Assays are performed in the presence and absence of an efflux transporter inhibitor or competitor. Efflux transporter inhibitors or competitors increase apical to basolateral transport and decrease basolateral to apical transport of compounds that are efflux transporter substrates. Apparent permeability ($P_{app}$) of test compounds is measured. Test compounds that are substrates of efflux transporters generate a $P_{app}$ (basolateral to apical)/$P_{app}$ (apical to basolateral) ratio of greater than 2.0, while test compounds that are not substrates generate a ratio of 1.5 or less. Test compounds that generate ratios between 1.5 and 2.0 require additional testing to determine if they are efflux transporter substrates. An agent, conjugate, or conjugate moiety that is a LAT1 substrate and also generates a ratio of greater than 2.0 can be modified. A modified agent, conjugate, or conjugate moiety that retains LAT1 substrate activity and generates a lower ratio compared to the unmodified agent, conjugate, or conjugate moiety indicates that the modified agent, conjugate, or conjugate moiety is a better candidate for retention inside the CNS.

An additional screen can be performed to determine whether agents, conjugates or conjugate moieties have substantial capacity for passive diffusion across the brain microvessel endothelial cells making up the blood brain barrier. Such an assay can be performed using cells lacking LAT1 transporters. That is, the agents, conjugates or conjugate moieties are exposed to cells that lack LAT1 transporters, and the amount of agents, conjugates or conjugate moieties that are present inside the cell is measured.

V. Modification of Compounds Having Non-Neuropharmacologic Activity

In some instances it is desirable to modify an agent to reduce its capacity to be transported from the blood into the brain. Reduced capacity to enter the brain is desirable for agents having a pharmacological activity that is useful in a tissue outside the CNS, but which causes undesired side effects when the agent enters the CNS. Most typically, such agents are drugs administered to treat a non-neurological disease, and which exert a useful therapeutic pharmacological effect on cells, tissues, or molecules located outside of the CNS. When such drugs are transported from the blood into the brain, serious side effects can occur. Many known drugs exhibit undesirable side effects from penetrating the CNS. Examples include drowsiness experienced by patients taking antihistamines, nonsteroidal anti-inflammatory drugs (NSAIDS), anti-asthmatics and antihypertensives.

The methods are performed on an agent having an intended site of pharmacological activity that is located outside of the CNS. The agent is known or suspected to enter the CNS. In some instances, the agent is known to be transported by LAT1. The agent is covalently attached to a conjugate moiety and the resulting conjugate is tested for transport into the brain. The assay can be performed on brain microvessel endothelial cells, cells transformed with a LAT1 expression vector, a polarized monolayer of cells, or an actual blood brain barrier via administration to a test animal. Transport of the conjugate is then compared with transport of the agent alone (i.e., without the conjugate moiety). Conjugates having a lower $V_{max}$ for transport than the agent alone are less likely to exhibit undesirable CNS side effects caused by unwanted transport from the blood into the brain. For example, preferred conjugates include those having a lower $V_{max}$ for transport by LAT1 than the agent alone.

Some methods comprise providing an agent having a pharmacological activity, wherein the pharmacological activity is useful for treating a disease present in a tissue other than the CNS, and the pharmacological activity results in undesired side effects in the CNS if the agent enters the CNS, modifying the agent, providing a cell expressing at least one transporter protein that transports substrates across the blood brain barrier, contacting the cell with the modified agent, and determining whether the modified agent passes through the plasma membrane via the transporter protein with a lower $V_{max}$ than the agent, a lower $V_{max}$ indicating that the modification decreases the capacity of the modified agent relative to the agent to cross the blood brain barrier, thereby decreasing undesired side effects in the CNS. In some methods the at least one transporter protein is LAT1. In some methods the cell is transformed or injected with a nucleic acid encoding a transporter or the cell is a brain microvessel endothelial cell. In some methods the modifying step comprises linking the agent to a conjugate moiety to form a conjugate, preferably wherein the conjugate moiety is an inhibitor of the LAT1 transporter.

Other methods comprise providing an agent having a pharmacological activity, wherein the pharmacological activity is useful for treating a disease present in a tissue other than the CNS, and the pharmacological activity results in undesired side effects in the CNS if the agent enters the CNS, modifying the agent, providing a cell expressing at least one efflux transporter protein that transports substrates out of the CNS, contacting the cell with the modified agent, and determining whether the modified agent is transported by the at least one efflux transporter protein with a higher $V_{max}$ than the agent, a higher $V_{max}$ indicating that the modification increases the capacity of the modified agent relative to the agent to be transported out of the CNS, thereby decreasing undesired side effects in the CNS. In some methods the at least one efflux transporter protein is P-glycoprotein (PgP), multidrug resistance protein (MRP1), or breast cancer resistance protein (BCRP). In some methods the cell is transformed or injected with a nucleic acid encoding an efflux transporter or the cell is a brain microvessel endothelial cell, a kidney-derived cell, or a uterine sarcoma cell. In some methods the modifying step comprises linking the agent to a conjugate moiety to form a conjugate, preferably wherein the conjugate moiety is a substrate of the efflux transporter.

VI. Sources of Neuropharmaceutical Agents, Imaging Components, and Conjugate Moieties Therapeutic neuropharmaceutical agents, cytotoxic neuropharmaceutical agents, imaging components and conjugate moieties can be obtained from natural sources such as, e.g., marine microorganisms, algae, plants, and fungi. Alternatively, these compounds can be from combinatorial libraries, including peptides or small molecules, or from existing repertoires of chemical compounds synthesized in industry, e.g., by the chemical, pharmaceutical, environmental, agricultural, marine, cosmeceutical, drug, and biotechnological industries. Neuropharmaceutical compounds can include proteins, antibiotics, adrenergic agents, anticonvulsants, small molecules, nucleotide analogs, chemotherapeutic agents, anti-trauma agents, peptides and other classes of agents used in treatment or prophylaxis of a neurological disease. Examples of such proteins include CD4 (including soluble portions thereof), growth factors (e.g., nerve growth factor and interferon), dopamine decarboxylase and tricosanthin. Examples of such antibiotics include amphotericin B, gentamycin sulfate, and pyrimethamine. Examples of such adrenergic agents (including blockers) include dopamine and atenolol. Examples of such chemotherapeutic agents include adriamycin, methotrexate, cyclophosphamide, etoposide, and carboplatin. An example of an anticonvulsant which can be used is valproate and an anti-trauma agent which can be used is superoxide dismutase. Examples of such peptides are somatostatin analogues and enkephalinase inhibitors. Nucleotide analogs which can be used include azido thymidine (hereinafter AZT), dideoxy Inosine (ddI) and dideoxy cytodine (ddc).

Typically if an agent is being screened as a substrate, the agent is known or suspected to have an inherent therapeutic neuropharmaceutical, cytotoxic neuropharmaceutical or imaging activity. If a conjugate is being screened, the conjugate usually comprises such an agent or component. If a conjugate moiety is being screened, the conjugate moiety typically lacks a therapeutic, cytotoxic or imaging activity and an agent or component that has this activity is added after screening.

Suitable cytotoxic agents for incorporation into conjugates or linkage to conjugate moieties after screening include platinum, nitrosourea, nitrogen mustard, nitroimidizole, and a phosphoramide group that is only cytotoxic to brain tumor cells. The choice of imaging component depends on the means of detection. For example, a fluorescent imaging component is suitable for optical detection. A paramagnetic imaging component is suitable for topographic detection without surgical intervention. Radioactive labels can also be detected using positron emission tomography or single photon emission computed tomography.

The agents, conjugates or conjugate moieties to be screened, optionally linked to a neuropharmaceutical agent or an imaging component if not inherently present, are preferably small molecules having molecular weights of less than 1000 Da and preferably less than 500 Da.

VII. Linkage of Neuropharmaceutical Agents or Imaging Components to Substrates

Conjugates can be prepared by either by direct conjugation of a neuropharmaceutical agent or an imaging component to a substrate of LAT1 with a covalent bond (optionally cleavable in vivo), or by covalently coupling a difunctionalized linker precursor with the neuropharmaceutical agent or imaging component and substrate. The linker precursor is selected to contain at least one reactive functionality that is complementary to at least one reactive functionality on the neuropharmaceutical agent or imaging component and at least one reactive functionality on the substrate. Optionally, the linker is cleavable. Suitable complementary reactive groups are well known in the art as illustrated below:

| COMPLEMENTARY BINDING CHEMISTRIES | | |
|---|---|---|
| First Reactive Group | Second Reactive Group | Linkage |
| hydroxyl | carboxylic acid | ester |
| hydroxyl | haloformate | carbonate |
| thiol | carboxylic acid | thioester |
| thiol | haloformate | thiocarbonate |
| amine | carboxylic acid | amide |
| hydroxyl | isocyanate | carbamate |
| amine | haloformate | carbamate |
| amine | isocyanate | urea |
| carboxylic acid | carboxylic acid | anhydride |
| hydroxyl | phosphorus acid | phosphonate or phosphate ester |

The same methods of chemical modification can be used to form conjugates for the purpose of inhibiting transport into the CNS, for inhibiting efflux from the CNS, or for enhancing efflux from the CNS.

VIII. Pharmaceutical Compositions

The above screening processes can identify one or more types of compounds that can be incorporated into pharmaceutical compositions. These compounds include agents that are both substrates for LAT1 and have an inherent neuropharmaceutical activity or imaging activity. The compounds also include conjugates in which a neuropharmaceutical agent or imaging component is linked to a substrate for LAT1. Conjugates comprising an agent with a pharmacological activity and a conjugate moiety having decreased substrate capacity for LAT1 relative to the agent alone are also provided for the purpose of reducing transport of the agent into the CNS, where the agent would confer undesired side effects.

One or more of the above entities can be combined with pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, buffered water, physiological saline, phosphate buffered saline (PBS), Ringer's solution, dextrose solution, and Hank's solution. In addition, the pharmaceutical composition or formulation can also include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents, detergents and the like (see, e.g., Remington's Pharmaceutical Sciences, Mace Publishing Company, Philadelphia, Pa., 17th ed. (1985); for a brief review of methods for drug delivery, see, Langer, Science 249:1527-1533 (1990); each of these references is incorporated by reference in its entirety).

Pharmaceutical compositions can be administered orally, intranasally, intradermally, subcutaneously, intrathecally, intramuscularly, topically, intravenously, or injected directly to a site of cancerous tissue. For parenteral administration, the compounds disclosed herein can be administered as injectable dosages of a solution or suspension of the compound in a physiologically acceptable diluent with a pharmaceutical carrier which can be a sterile liquid such as water, oils, saline, glycerol, or ethanol. Additionally, auxiliary substances, such as wetting or emulsifying agents, surfactants, pH buffering substances and the like can be present in the pharmaceutical compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or a copolymer thereof for enhanced adjuvant effect, as discussed above (see Langer, Science 249, 1527 (1990) and Hanes, Advanced Drug Delivery Reviews 28, 97-119 (1997). The pharmaceutical compositions disclosed herein can be administered in the form of a depot injection or implant preparation which can be formulated in such a manner as to permit a sustained or pulsatile release of the active ingredient.

Pharmaceutical compositions for oral administration can be in the form of e.g., tablets, pills, powders, lozenges, sachets, cachets, elixirs, suspensions, emulsions, solutions, or syrups. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methylcellulose. Preserving agents such as methyl- and propylhydroxy-benzoates; sweetening agents; and flavoring agents can also be included. Depending on the formulation, compositions can provide quick, sustained or delayed release of the active ingredient after administration to the patient. Polymeric materials can be used for oral sustained release delivery (see "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Ranger and Peppas, 1983, J. Macromol. Sci. Rev. Macromol Chem. 23:61; see also Levy et al., 1985, Science 228:190; During et al., 1989, Ann. Neurol. 25:351; Howard et al., 1989, J. Neurosurg. 71:105). Sustained release can be achieved by encapsulating conjugates within a capsule, or within slow-dissolving polymers. Preferred polymers include sodium carboxymethylcellulose, hydroxypropylcellulose, hydroxypropylmethylcellulose and hydroxyethylcellulose (most preferred, hydroxypropyl methylcellulose). Other preferred cellulose ethers have been described (Alderman, Int. J. Pharm. Tech. & Prod. Mfr., 1984, 5(3) 1-9). Factors affecting drug release have been described in the art (Bamba et al., Int. J. Pharm., 1979, 2, 307). For administration by inhalation, the compounds for use according to the disclosures herein are conveniently delivered in the form of an aerosol spray preparation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

Effective dosage amounts and regimes (amount and frequency of administration) of the pharmaceutical compositions are readily determined according to any one of several well-established protocols. For example, animal studies (e.g., mice, rats) are commonly used to determine the maximal tolerable dose of the bioactive agent per kilogram of weight. In general, at least one of the animal species tested is mammalian. The results from the animal studies can be extrapolated to determine doses for use in other species, such as humans for example.

The components of pharmaceutical compositions are preferably of high purity and are substantially free of potentially harmful contaminants (e.g., at least National Food (NF) grade, generally at least analytical grade, and more typically at least pharmaceutical grade).

To the extent that a given compound must be synthesized prior to use, the resulting product is typically substantially free of any potentially toxic agents, particularly any endotoxins, which may be present during the synthesis or purification process. Compositions are usually made under GMP conditions. Compositions for parenteral administration are usually sterile and substantially isotonic.

IX. Methods of Treatments

Pharmaceutical compositions disclosed herein are used in methods of treatment of prophylaxis of neurological diseases. Examples of such diseases amenable to treatment are cancer (e.g., brain tumors), Acquired Immune Deficiency Syndrome (AIDS), stroke, epilepsy, Parkinson's disease, multiple sclerosis, neurodegenerative disease, trauma, depression, Alzheimer's disease, migraine, pain, seizure disorders, inflammation, and allergic diseases.

Other pharmaceutical compositions disclosed herein are used in methods of treatment and prophylaxis of non-neurological diseases. Examples of such diseases amenable to treatment are cancer (e.g., tumors of non-CNS tissue), inflammation, and allergic diseases.

In prophylactic applications, pharmaceutical compositions are administered to a patient susceptible to, or otherwise at risk of, a disease in an amount and frequency sufficient to eliminate or reduce the risk, lessen the severity, or delay the outset of the disease, including biochemical, histologic and/or behavioral symptoms of the disease, its complications and intermediate pathological phenotypes presenting during development of the disease. In therapeutic applications, pharmaceutical compositions are administered to a patient suspected of, or already suffering from such a disease in an amount and frequency sufficient to cure, or at least partially arrest, the symptoms of the disease (biochemical, histologic and/or behavioral), including its complications and intermediate pathological phenotypes in development of the disease. An amount of pharmaceutical composition sufficient to achieve at least one of the above objects is referred to as an effective amount, and a combination of amount and frequency sufficient to achieve at least one of the above objects is referred to as an effective regime.

X. Methods of Imaging

As discussed above, the invention provides conjugates comprising a conjugate moiety, which is a substrate of LAT1, linked to an imaging component, as well as agents that are substrates for LAT1 and have an inherent imaging activity. Optionally, the agents also have inherent affinity for a particular antigen or cell type found in the CNS, or the conjugate is provided with an additional conjugate moiety having such affinity. The additional moiety is referred to as a targeting moiety. The targeting moiety can be an antibody or fragment thereof, or any other molecule that specifically binds to a desired antigen or cell type within the brain. The invention further provides pharmaceutical compositions comprising all of these entities. These pharmaceutical compositions can be used for in vivo imaging. The compositions are administered to a patient and preferentially taken up by central nervous system cells after being actively transported from the blood into the brain by brain microvessel endothelial cells expressing LAT1 in the patient. The imaging activity is then detected. In some methods, the imaging component is also a cytotoxic agent. For example many radioisotopes are suitable for both imaging and tumor cytotoxic activity. In such cases, methods of imaging and methods of treatment can be combined. Currently used diagnostic imaging techniques include positron emission tomography (PET), magnetic resonance imaging (MRI), and computed tomography (CT). Actively transported imaging components provide information about, for example, the presence and/or size of a brain tumor. The cell assay methods provided herein can also be used to identify imaging compounds for use outside the CNS, wherein such imaging agents exert undesirable side effect on the CNS.

As can be appreciated from the disclosure above, the present invention has a wide variety of applications. For example, the LAT1 transporter can be used to identify an agent or conjugate that is a substrate for the transporter and that can cross the blood brain barrier and can therefore treat the CNS. The LAT1 transporter also can be used to increase the capacity of an agent to cross the blood brain barrier by identifying a conjugate moiety that is a substrate for the LAT1 transporter and linking the conjugate moiety to the agent. Accordingly, the following examples are offered by way of illustration, not by way of limitation.

EXAMPLES

Example 1

Quantitative PCR Detection of LAT1 Expression in Brain Endothelial Cells

Quantitative PCR was performed to analyze LAT1 expression in human, mouse and rat brain endothelial cells. Endothelial cells from mouse and rat brains were isolated as follows: To isolate an adequate number of brain endothelial cells, brains were removed from 10 adult rats or 20 adult mice. The brains were washed in 70% ethanol, and placed in sterile phosphate buffered saline. Meninges and surface vessels were removed. Cortical gray matter was minced, placed in preparation medium (1 g/L glucose, 25 mM HEPES, 100 U/ml penicillin, 100 µg/ml streptomycin, 10 µg/ml DNAse I, 1 mg/ml collagenase/dispase, in DMEM, adjusted to a pH of 7.4) and incubated for 1 hour at 37° C. Samples were centrifuged for 10 minutes at 1000×g. Fat, cell debris, and myelin were discarded. The pellet was resuspended in fresh preparation medium and incubated for an additional 3 hours at 37° C. in a shaking bath. Medium was filtered through a 230 µM nylon sieve followed by a 150 µM nylon sieve. Microvessels were collected by retention on a 60 µM nylon sieve. Capillaries were washed with preparation medium, and then pelleted for RNA isolation.

Human brain tissue was obtained from epileptic foci surgically removed from human patients. Human brain microvessel endothelial cells were isolated essentially as described above.

Total RNA was isolated from the brain endothelial cells using the standard protocol for the RNEasy RNA Isolation Kit (Qiagen). Cells were resuspended in RLT lysis buffer at 10 mls per 0.4 grams of cells. Lysates were vortexed and run through a QiaShredder Column (Qiagen) prior to RNA isolation. Once isolated, the RNA was quantified, run on a 1% agarose gel to ensure integrity, and then stored at −80° C.

Prior to cDNA synthesis, total RNA was DNAse I treated to destroy genomic DNA contamination (Invitrogen DNAseI Kit). Twenty microliters of oligo dT primed single-stranded cDNA was then synthesized from 1 µg total RNA (Invitrogen Thermoscript cDNA Synthesis Kit). The cDNA was treated with RNAse H and stored at −20° C.

Quantitative PCR was performed in a 96-well format using the MJ Research DNA Engine Opticon. For each transporter, a pair of 26 base oligonucleotide primers were used to amplify the specific transporter. Primers were designed to recognize the non-conserved 3' ends of LAT1 transporter mRNA. The single stranded cDNA was used as a template for a PCR reaction containing human, mouse or rat primers and SYBR Green master mix (Applied Biosystems). Fluorescent signal was read and graphed each cycle. A CT value, or cycle threshold value, was determined for each reaction. This value was defined as the point at which the fluorescent signal of the reaction exceeds background fluorescence. Background fluorescence was calculated as 20 standard deviations above the average signal from cycles 3 through 10. Transcript abundance was normalized to GAPDH levels. Averaged results from several experiments in which rat LAT family transporters with similar substrate specificity were amplified are shown below in Table 2. The units of measurement are mRNA transcripts detected per PCR reaction. Results from two mouse LAT1 amplification experiments are shown below in Table 3. Averaged results from 2 human LAT1 amplification experiments are shown below in Table 4.

TABLE 2

| LAT family mRNA Expression in Rat Capillary Endothelial Cells | | | |
|---|---|---|---|
| Gene | transcripts | forward primer | reverse primer |
| LAT1 | 22,781 | gaggaggcagaggtcaaggtcagagt (SEQ ID NO:3) | aaaaacctacagatgggcgtcctcag (SEQ ID NO:4) |

TABLE 2-continued

LAT family mRNA Expression in Rat Capillary Endothelial Cells

| Gene | transcripts | forward primer | reverse primer |
|---|---|---|---|
| LAT2 | 2,408 | gaggctgagtttgggctgaattgtgg (SEQ ID NO:5) | ggtgcaggctgaaggaatgggaggaa (SEQ ID NO:6) |
| Y + LAT1 | 485 | agcctgttcttccccatcgtcttctg (SEQ ID NO:7) | cgatgccgatgagggagttgatggta (SEQ ID NO:8) |
| BAT | 218 | ttttatttccaaccgtgcatgctact (SEQ ID NO:9) | attcctgaggcccttgcatgtgtgat (SEQ ID NO:10) |
| LAT-ASC | 140 | tcggcatcatcattatcctcactggg (SEQ ID NO:11) | ggggtaaaccacgaaacacagctcct (SEQ ID NO:12) |

TABLE 3

LAT1 mRNA Expression in Mouse Capillary Endothelial Cells

| Mouse LAT1 | transcripts | forward primer | reverse primer |
|---|---|---|---|
| Exp. #1 | 28,657 | actgccctgaaagacacccctac ctg (SEQ ID NO:13) | caaaaagcctcacaaaacagcag acc (SEQ ID NO:14) |
| Exp. #2 | 16,906 | " | " |
| Exp. #2 | 16,347 | " | " |

To confirm the purity of the brain endothelial cell RNA preparations, samples of RNA from each preparation were tested by quantitative PCR for mRNA transcript levels of capillary (GLUT1), neuronal (BNPI) and glial (GFAP) cell markers. The quantitative PCR analysis was conducted as described above. The primers used are shown in Table 6 below. The results of the control gene transcript quantitation are shown in Table 7 below.

TABLE 4

LAT1 mRNA Expression in Human Capillary Endothelial Cells

| Human LAT1 | transcripts | forward primer | reverse primer |
|---|---|---|---|
| Exp. | 188,083 | tgggacgtggacatgcctcaaggata (SEQ ID NO:15) | gggcacacagcaccaaggatcacaga (SEQ ID NO:16) |

The enrichment of LAT1 transcripts in brain capillary endothelial cells (BMECs) relative to total brain transcripts was also determined by quantitative PCR as described above. Total RNA was isolated from whole brain samples. LAT1 transcript levels were normalized to GLUT1 transcript levels. GLUT1 transcript levels were determined using the human, mouse and rat GLUT1 primers described in Table 7 below. Table 5 below shows the average LAT1 transcript levels, normalized transcript levels, and ratio of LAT1 transcripts in BMEC versus brain in human, mouse and rat brain.

TABLE 5

LAT1 mRNA Expression in Human, Mouse and Rat Brain Microvessel Endothelial Cells

| | Average BMEC | | | BMEC % GLUT1 | | | BMEC:Brain Ratio | | |
|---|---|---|---|---|---|---|---|---|---|
| | Human | Mouse | Rat | Human | Mouse | Rat | Human | Mouse | Rat |
| LAT1 | 169,370 | 16,347 | 24,545 | 21.1 | 9.6 | 18.1 | 13.9 | 3.2 | 3.0 |
| GLUT1 | 802,859 | 169,616 | 135,976 | 100 | 100 | 100 | 43.1 | 3.1 | 9.2 |

TABLE 6

Primers for Quantitative Analysis of Control Genes

| Gene | forward primer | reverse primer |
|---|---|---|
| Human GLUT1 | ggggcatgattggctccttctctgtg (SEQ ID NO:17) | aggccgcagtacacaccgatgatgaa (SEQ ID NO:18) |
| Mouse GLUT1 | cgcccattcctgtctcttcctaccca (SEQ ID NO:19) | tcatggtgtttgtgtggccctcagtg (SEQ ID NO:20) |
| Rat GLUT1 | gaaccacagggaaagcaactctaatc (SEQ ID NO:21) | tcgggtcattattttcacgtttcca (SEQ ID NO:22) |
| Human BNPI | cacccccgctttcctttatctccag (SEQ ID NO:23) | ctgctggtagggagatgtgaagtgg (SEQ ID NO:24) |
| Mouse BNPI | acggggacatcactcagaattacat (SEQ ID NO:25) | ttcttccttttctcccagccgttag (SEQ ID NO:26) |
| Rat BNPI | gccacacacagcacagttcagcctcc (SEQ ID NO:27) | ggacagcactgggcaagggaagac (SEQ ID NO:28) |
| Mouse GFAP | aggaaattgctggagggcgaagaaaa (SEQ ID NO:29) | caccatcccgcatctccacagtcttt (SEQ ID NO:30) |
| Rat GFAP | ggtgggcaggtgaggaagaaatggag (SEQ ID NO:31) | tagcagaggtgacaaggggggagtg (SEQ ID NO:32) |

TABLE 7

Control Gene mRNA Transcript Levels

| Control Gene | Source | Control Gene mRNA Transcript Abundance | | |
|---|---|---|---|---|
| | | Human | Rat | Mouse |
| GLUT1 (Capillary marker) | Capillaries | 802859 | 169616 | 135976 |
| | Whole Brain | 11120 | 13546 | 5278 |
| BNPI (Neuronal marker) | Capillaries | 2614 | 5 | 343 |
| | Whole Brain | 222285 | 67705 | 122509 |
| GFAP (Glial marker) | Capillaries | Not determined | 561 | 670 |
| | Whole Brain | Not determined | 68789 | 24032 |

Example 2

Studies of Cloned LAT1 Transporters: Oocyte Expression

To assess transport function of a specific transporter protein, it can be desirable to clone the cDNA and express the protein in cells that have low endogenous transport activity. Human LAT1 was cloned by PCR, fully sequenced, and subcloned into plasmids that can be used for expression in mammalian cells or Xenopus oocytes. The co-subunit required for LAT1 function, 4F2HC (Genbank accession AB018010), was also cloned and sequenced. Unless otherwise noted, 4F2HC was also co-expressed in each heterologous system described in the example. Because many mammalian cell lines exhibit high levels of amino acid transport activity, expression in Xenopus oocytes can be advantageous due to the low levels of endogenous amino acid transport. For expression in Xenopus oocytes, in vitro LAT1 and 4F2HC cRNA was prepared and injected into defoliculated oocytes.

Figure 2:
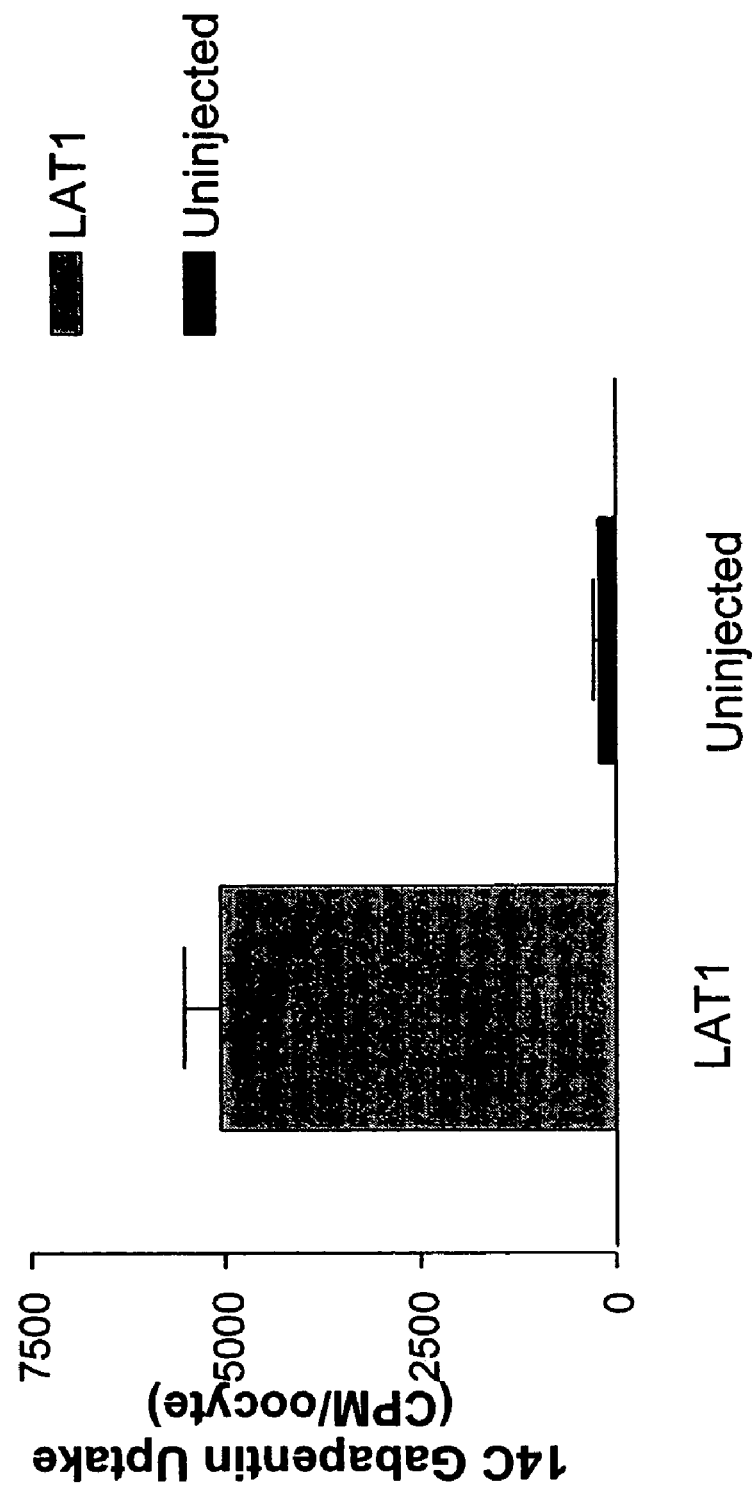
FIG. 2 shows uptake of $^{14}$C-gabapentin into oocytes injected or not injected with a LAT1 expression vector.
Figure 3:
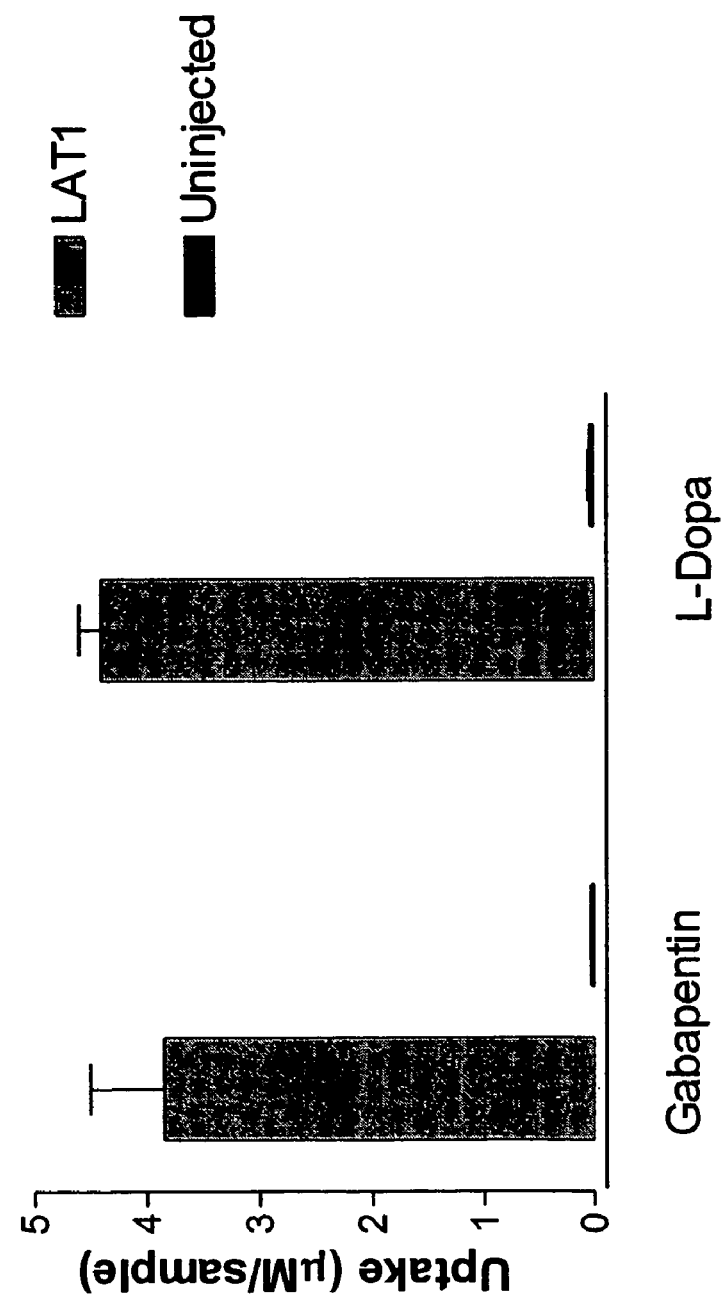
FIG. 3 shows uptake of gabapentin and L-dopa into oocytes injected with LAT1 and 4F2HC cRNA.

Oocytes expressing LAT1 and 4F2HC exhibited higher levels of $^3$H-L-dopa uptake than noninjected controls, as shown in FIG. 2. To measure directly the uptake of possible substrates, an oocyte uptake assay in which compounds are measured by mass spectroscopy was developed. To illustrate this approach, uptake assays of gabapentin and L-dopa were performed. Oocytes used in this experiment were injected with LAT1 cRNA and incubated at 16-18° C. until maximal transporter expression was reached. Oocytes from the same batch, which were not injected with cRNA, were used in the experiment to serve as a control. 1 mM solutions of gabapentin and L-dopa were prepared in oocyte ringers (ND96) buffer (90 mM NaCl, 10 mM HemiNa HEPES, 2 mM KCl, 1 mM $MgCl_2$, 1.8 mM $CaCl_2$) containing 0.5% bovine serum albumin. The gabapentin and L-dopa were then separately administered to pools of 8 oocytes for a 4 min duration. Following the incubation, the pools of oocytes were washed 4 times with 0.5% BSA ND96 buffer and separated into 2 oocyte subpools containing 4 oocytes each. Subpools were homogenized in 150 µl of ice cold 80% MeOH/$H_2O$, and lysed manually with a P200 pipettor. Lysates were vortexed briefly before being spun in a 4° C. tabletop centrifuge at 13.2 krpm for 15 minutes. Approximately 110 µl of lysate was removed from the eppendorf tubes and placed in a 96-well plate. Lysates were analyzed for gabapentin and L-dopa by liquid chromatography-mass spectroscopy. An example of LC-MS-MS compound uptake in oocytes is shown in FIG. 3.

Samples were analyzed by LC-MS-MS as follows. A specific method was developed for each compound, and calibrated against a series of dilutions of known compound concentrations spiked into cellular extract. Typically compound methods were linear over the concentration range 0.1 to 10 mM. Measurements were performed using an API 2000 LC-MS-MS spectrometer equipped with Agilent 1100 binary transporters and a CTC HTS-PAL autosampler. Analyte fragmentation peaks were integrated using Analyst 1.2 quantitation software, and concentrations were calculated using a calibration curve of signals produced by known concentrations of the compound.

Example 3

Studies of Cloned LAT1 Transporters: Uptake into Mammalian Cells

To increase the throughput of LAT1 compound screening, a mammalian cell assay was developed. Because LAT1 mRNA is expressed at detectable levels in many cancer cell lines, over 20 human cell lines were screened for LAT1 expression using quantitative PCR. Cell lines included A498, A549, ASPC, CALU, CAPAN, DLD, DU145, H69AR, HCT8, HEK, HELA, HEPG2, HL60, JAR, JUR, KB, LOVO, MCF7, PANC1, PC3, and SW48. The KB cell line was found to have the highest levels of LAT1 mRNA and lacked expression of other transporters for large neutral amino acids. KB cells exhibited high levels of $^{14}$C-gabapentin transport that was not sodium dependent and was inhibited by known LAT1 substrates with affinities similar to cloned human LAT1 protein.

Figure 4:
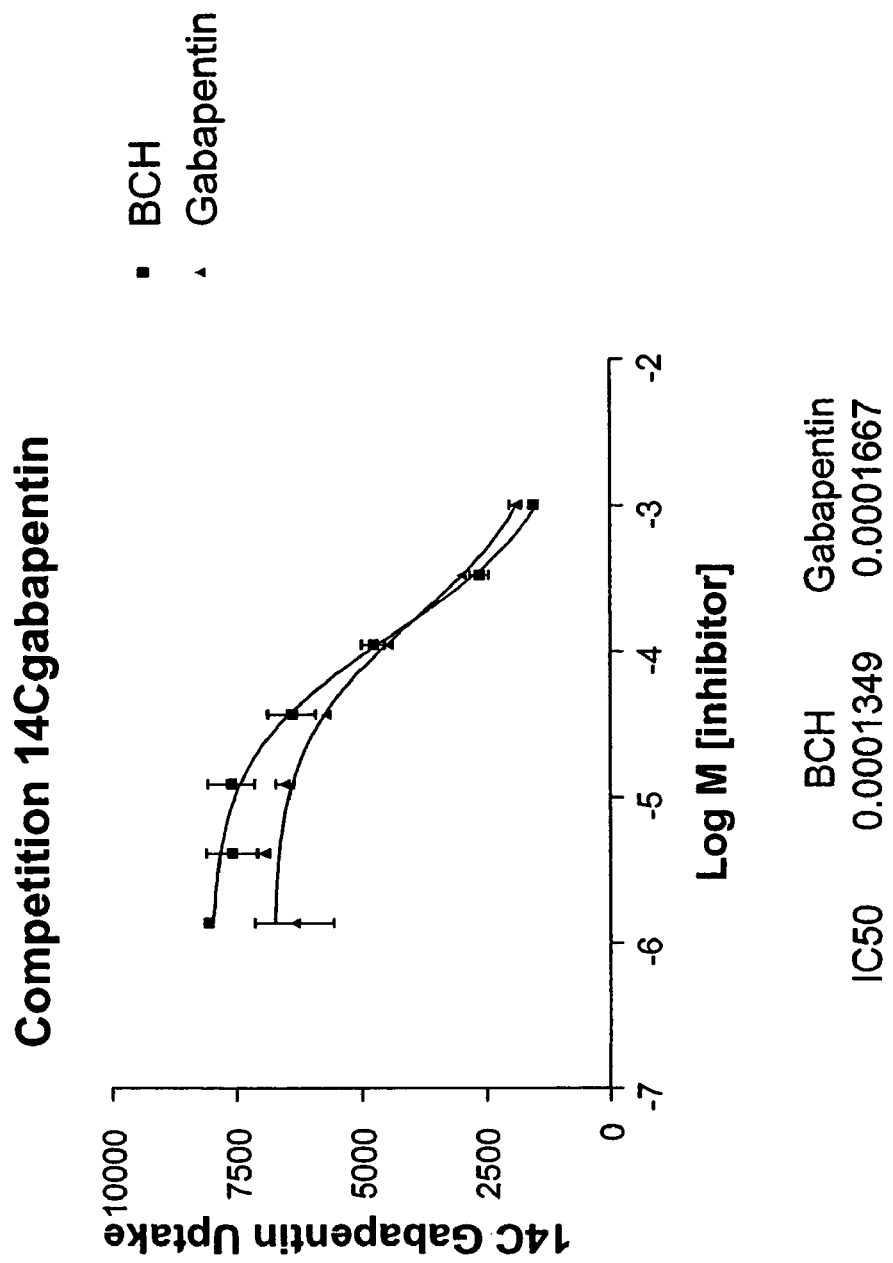
FIG. 4 shows competition for uptake of $^{14}$C-gabapentin into KB cells by BCH and gabapentin.

To determine whether a compound interacts with the LAT1 transporter, a competition-binding assay was developed. The assay measures how different concentrations of a test compound block the uptake of a radiolabeled substrates such as $^{14}$C-L-dopa or $^{14}$C-gabapentin. The half-maximal inhibitory concentration ($IC_{50}$) for inhibition of transport of a substrate by a test compound is an indication of the affinity of the test compound for the LAT1 transporter. Competition binding studies were performed as follows. KB cells were plated in 96-well plates at 100,000 cells/well and incubated for 24 hours at 37° C. Radiolabeled $^{14}$C-gabapentin (~50,000 cpm/well) was added to each well in the presence and absence of various concentrations of test compound in duplicate or triplicate. Plates were incubated at room temperature for 20 min. Excess radiolabeled substrate was removed and cells were washed three times with a 96-well plate washer with cold assay buffer. Scintillation fluid was added to each well, the plates were sealed and counted in a 96-well plate-based scintillation counter. Data were graphed and analyzed using non-linear regression analysis with Prism Software (GraphPad, Inc., San Diego, Calif.). An example of results from the competition assay is shown in FIG. 4. The figure shows uptake of radiolabeled gabapentin into KB cells and competition with unlabeled gabapentin and bicyclohexane amino acid (BCH).

Example 4

Studies of Cloned LAT1 Transporters: Substrate Identification

Figure 5:
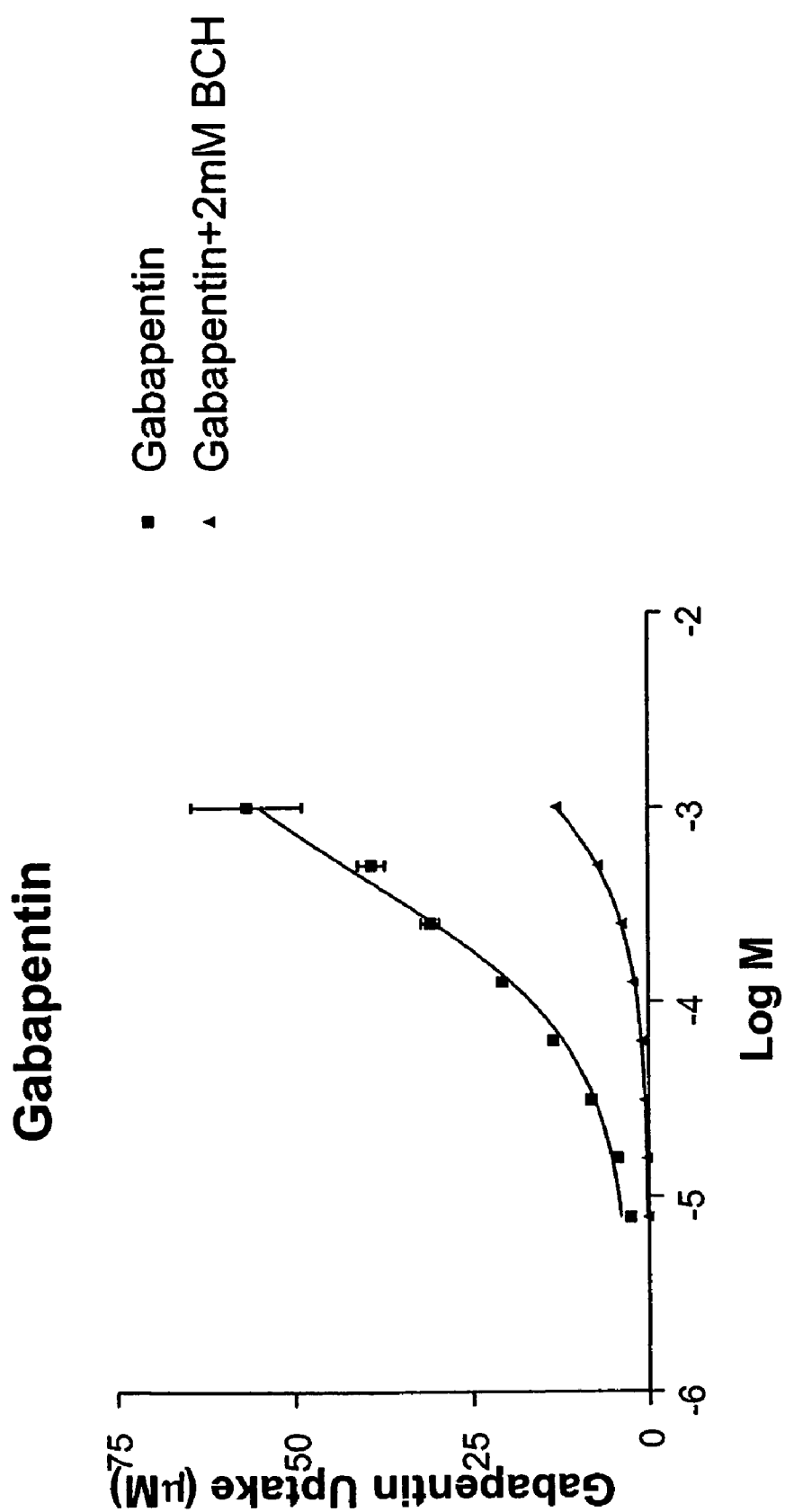
FIG. 5 shows uptake of different concentrations of gabapentin into KB cells and that gabapentin uptake is inhibited by BCH.

Competition binding studies only demonstrate that a molecule interacts with the LAT1 protein, but do not demonstrate whether the molecule is a substrate and is translocated across the plasma membrane or is non-transported inhibitor or a non-transported ligand. In order to measure whether test compounds are actively translocated across the plasma membrane by LAT1, and to determine the maximal transport rate, a direct uptake method was developed that utilizes mass spectroscopy. For direct uptake measurements using mass spectroscopy, KB cells were prepared similarly to those used for competition studies (described above). To measure transport of a test compound such as gabapentin, KB cells were washed and incubated with test compounds for 5 minutes. Excess substrate was removed by washing with cold assay buffer. Cells were lysed with 50% ethanol/water and the cell debris was pelleted by centrifugation. The supernatant was analyzed by LC-MS-MS. As a negative control, uptake was measured in cells that were simultaneously exposed to phenylalanine (100 mM) to block LAT1 transport. Typically, uptake levels of a test compound are compared to uptake of an optimal LAT1 substrate such as L-dopa or gabapentin. An example of results from this assay is shown in FIG. 5.

Example 5

Studies of Cloned LAT1 Transporters: LAT1 Exchange Assay

Figure 6:
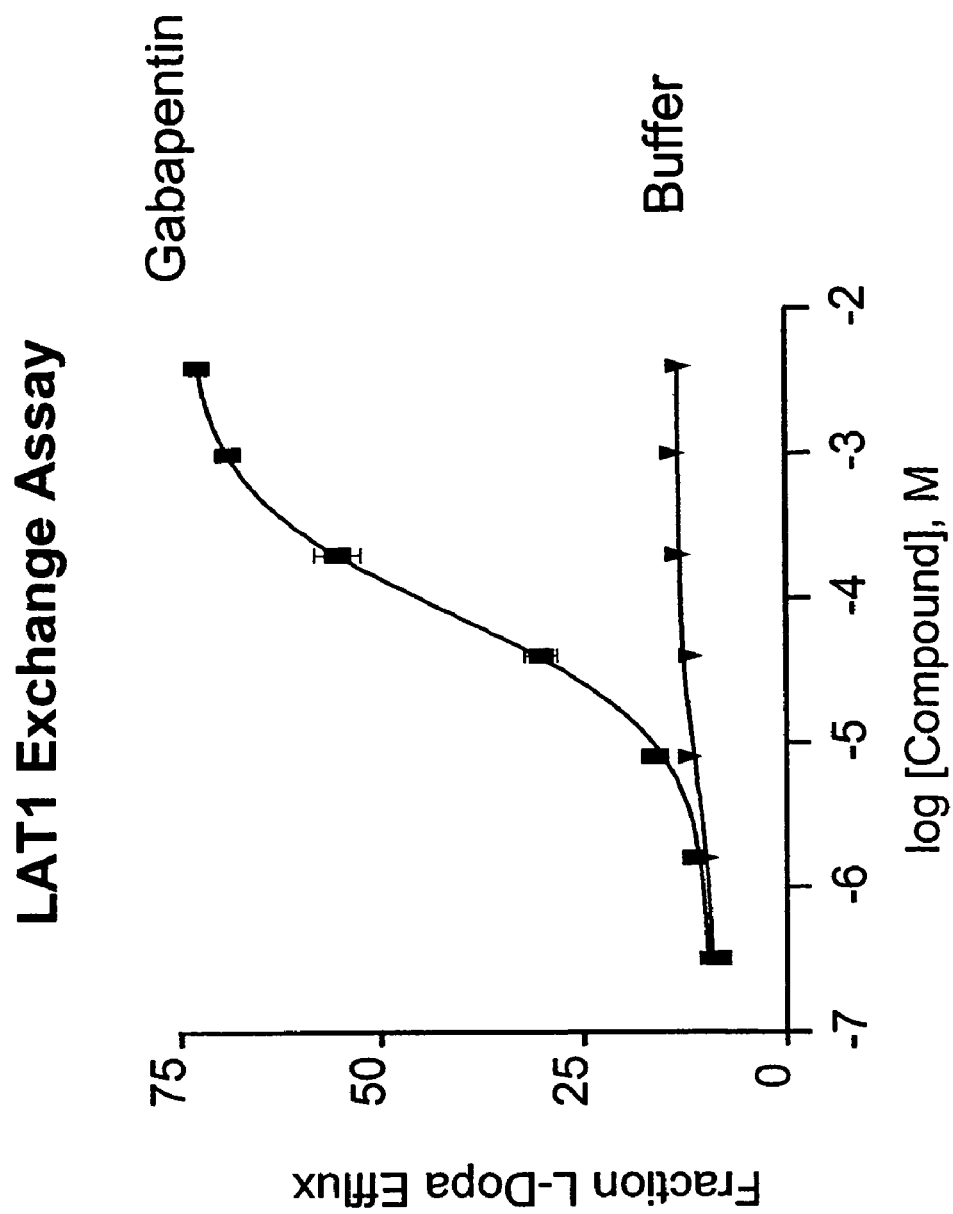
FIG. 6 shows measurement of LAT1 transport by an exchange assay.

For more rapid determination of whether a compound is a LAT1 substrate, a high-throughput 96-well based heteroexchange assay for LAT1 was developed. The assay is based on the fact that LAT1 is an obligate exchange protein, meaning that uptake of one substrate molecule is linked to the efflux another substrate molecule. The assay measures the stimulated release of $^{14}$H-L-dopa from cells in response to uptake of a test compound. KB cells expressing LAT1 were plated at 100,000 cells/well and incubated at 37° C. for 24 hours. Cells were then loaded with $^{14}$H-L-dopa, and radiolabeled compound in the media was removed. Test compounds such as gabapentin were then added to each well, and an aliquot of the media was removed 2 minutes later and tested for the presence of $^{14}$H L-Dopa. In the absence of a substrate L-Dopa is not released into the media, but a LAT1 substrate causes the release of more than 50% of L-Dopa from the cells in 2 minutes. By varying the concentration of test compound the EC50 can be calculated, and the $V_{max}$ can be determined as a fraction of the efflux induced by saturating concentrations of an optimal substrate such as L-dopa. An example of results of this assay is shown in FIG. 6.

Example 6

Efflux Assays

Figure 7:
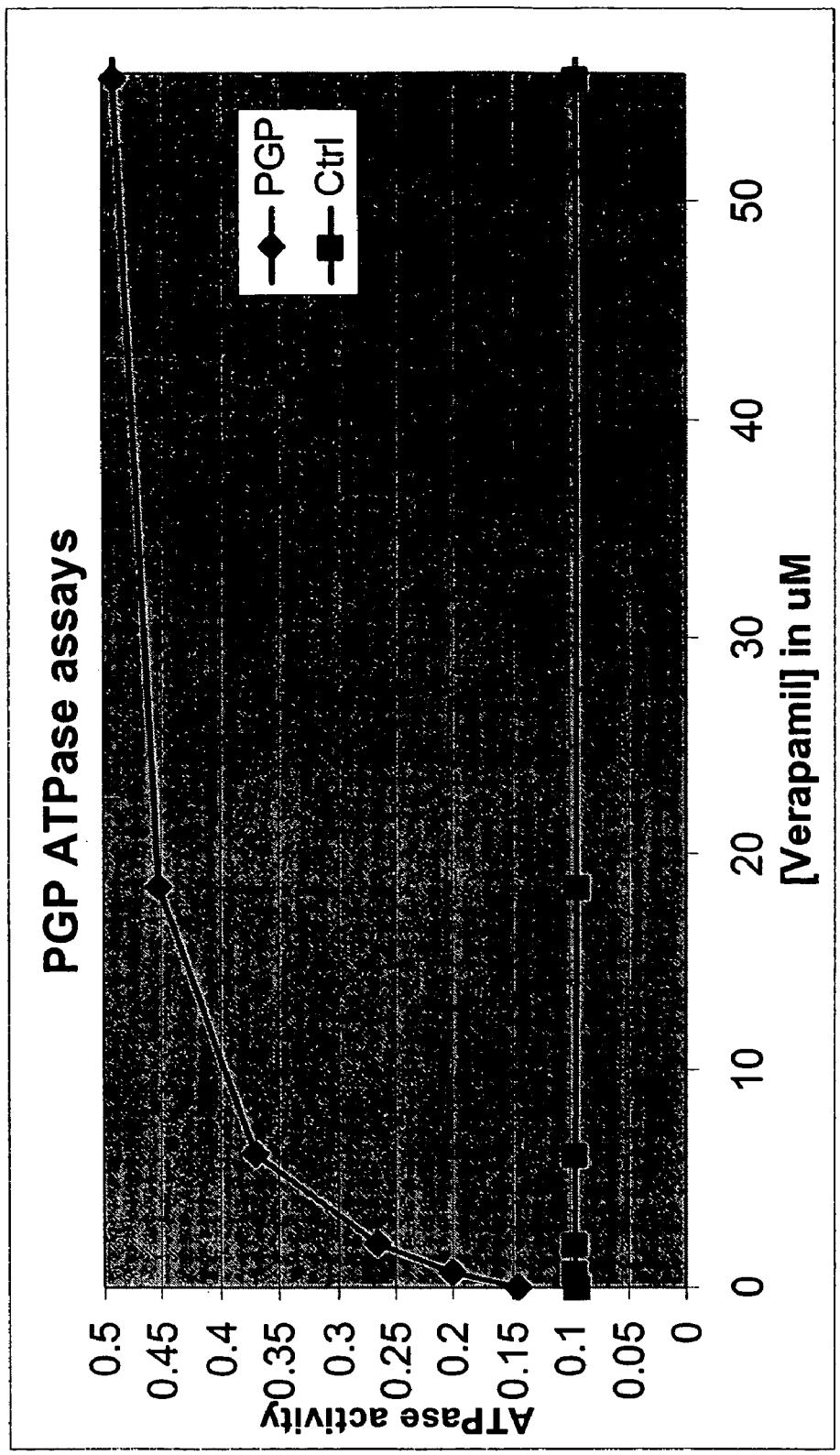
FIG. 7 shows an efflux transporter ATPase activity assay using membrane preparations containing the PgP efflux transporter and the PgP substrate verapamil.

FIG. 7 depicts the results of an efflux experiment in which the PgP substrate verapamil was added to commercial Baculovirus membranes (purchased from BD Biosciences) at various concentrations depicted on the X axis followed by ATPase activity measurement. The ATPase activity measurement was performed using the lactate dehydrogenase/pyruvate kinase coupled enzyme system described by Tietz & Ochoa, Arch. Biochim. Biophys. Acta 78:477 (1958) to follow the decrease in absorbance at 340 nm resulting from the oxidation of NADH, which is proportional to ATPase activity. 5 mM sodium azide ($NaN_3$), 1 mM EGTA, and 0.5 mM Ouabain, each of which inhibit non-specific ATPases in the membranes, were added to the reactions to further enhance the specificity of the PgP ATPase signal. The other components in the assay mixture were 25 mM Tris, pH 7.8, 100 mM NaCl, 10 mM KCl, 5 mM $MgCl_2$, 1 mM DTT, 2 mM phosphoenolpyruvate, 1 mM NADH, 0.1 mg/ml lactate dehydrogenase, 0.1 mg/ml pyruvate kinase, 5 mM ATP, and 6 µg PgP or control membranes. FIG. 7 demonstrates that as the concentration of verapamil was increased, the ATPase activity in PgP-containing membranes but not in control membranes also increased.

Figure 8:
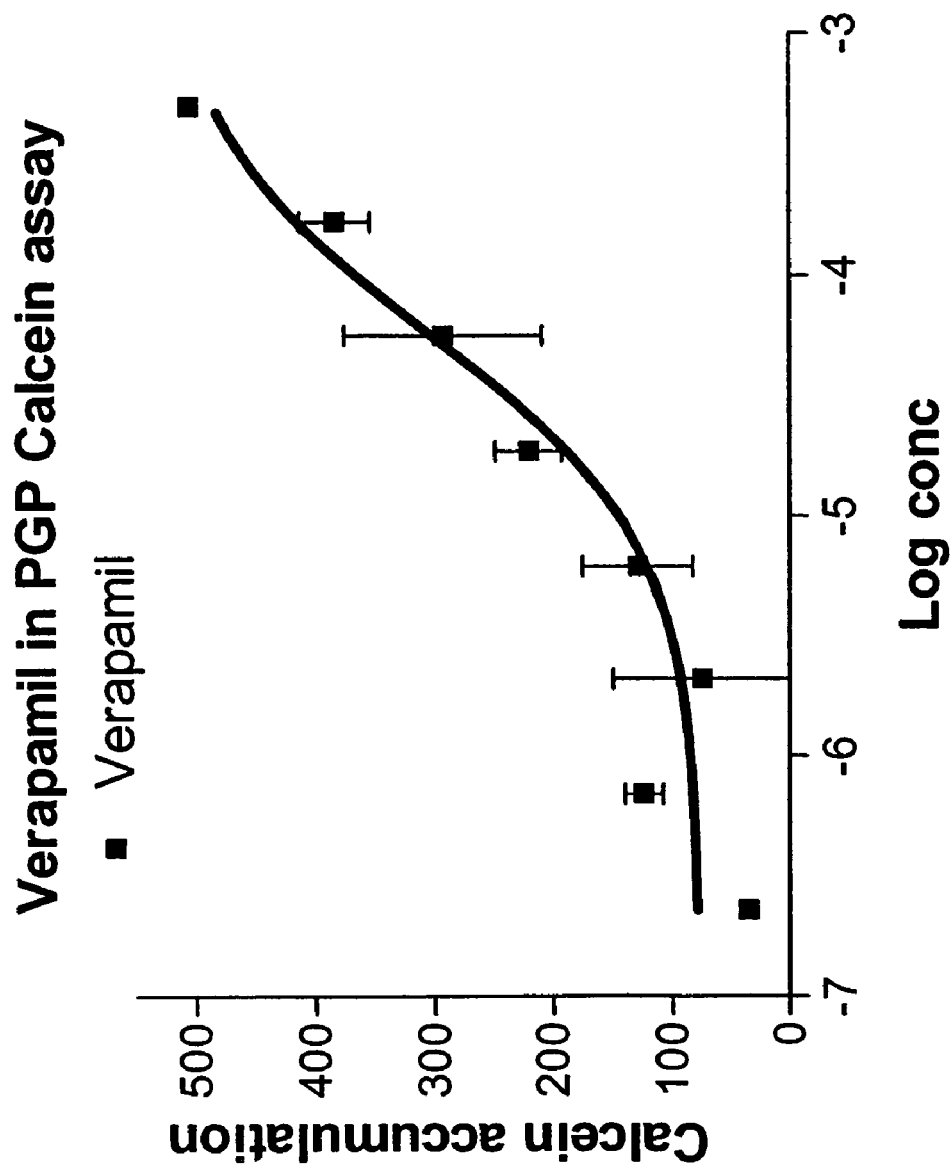
FIG. 8 shows an efflux transporter competition assay using the reporter molecule calcein-AM and the PgP substrate verapamil.

FIG. 8 depicts the results of an efflux competition assay. A tetracycline-inducible PgP expression construct (TREx-PgP, made using the TREx plasmid, Invitrogen, Carlsbad, Calif.) was transfected into HEK cells. The cells were incubated with PgP substrate 5 µM calcein-AM, which passively diffuses into the cells, as well as with various concentrations of the PgP substrate verapamil as shown in FIG. 8. As the concentration of PgP substrate verapamil was increased, more calcein-AM accumulated in the cells and was converted to the fluorescent product calcein.

Figure 9:
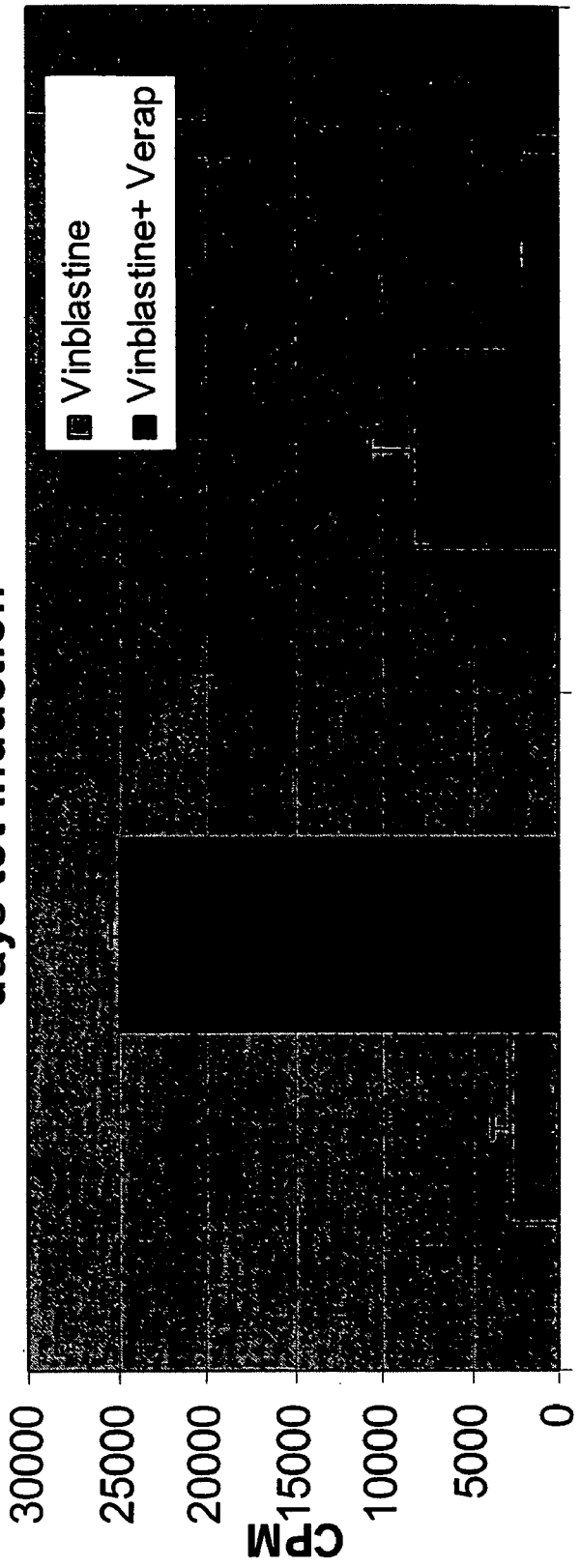
FIG. 9 shows a direct efflux transport assay using a polarized monolayer of MDCK cells transfected with a tetracycline-inducible PgP expression construct.

FIG. 9 depicts the results of a cellular transwell monolayer efflux assay. MDCK cells transfected with the tetracycline-inducible TREx-PgP expression vector were seeded on polycarbonate filter membranes in transwell dishes and grown for 3-5 days, yielding a polarized monolayer with tight junctions between cells. In this example, apical to basolateral and basolateral to apical transport of 2.5 nM (approximately 100,000 cpm) radiolabeled PgP substrate $^3$H-vinblastine was measured in the absence and presence of 250 μM of the inhibitor/competitor verapamil. The left set of bars depicts apical to basolateral transport, while the right set of bars depicts basolateral to apical transport. Apical to basolateral transport of $^3$H-vinblastine was strongly increased and basolateral to apical transport of $^3$H-vinblastine was strongly decreased in the presence of verapamil, indicating that $^3$H-vinblastine is a substrate of PgP.

Example 7

Recombinant LAT1 Expression

An inducible tet promoter-LAT1-4F2HC fusion protein expression construct was prepared. 4F2HC is a glycoprotein that co-assembles with LAT1. The tet promoter-LAT1-4F2HC expression construct was prepared using the Gateway plasmid cloning system following manufacturers instructions (Invitrogen), with the following variations: The tet-LAT1-4F2hc fusion protein expression construct was transfected into HEK-TREx cells using Fugene transfection following manufacturers instructions (Roche Biosciences). The resulting cell line was designated a HEK-TREx LAT1-4F2hc inducible cell line.

Example 8

LAT1 Competition Uptake Assay

A competition assay was developed to determine the ability of a test compound(s) to inhibit the uptake of radiolabeled substrates into HEK-TREx-LAT1-4F2hc cells induced to over-express hLAT1. The results are stated as affinities ($IC_{50}$).

Competition uptake assays were prepared as follows: Compounds were prepared for the competition assay by diluting a 100 mM stock concentration of a compound (in DMSO) to the appropriate working concentration. Typically, a seven-point dose response curve was prepared starting at a final assay concentration of 1-5 mM and carrying out three-fold dilutions. These dilutions were prepared by making a working "compound" plate that contains a 2× solution of the desired starting concentration of each test compound in duplicate in row A of a v-bottom microtiter plate. Six 3-fold serial dilutions (from row B to G) were made into the HBSS assay buffer (9.8 g/L Hank's Balance Salts (Sigma; H-1387), 2.6 g/L HEPES (10 mM) (Sigma; H-3375), 0.35 g/L NaHCO$_3$ (4.2 mM) (Sigma; S-6297), pH to 7.4 with 5N NaOH) (with the appropriate amount of DMSO so that the DMSO concentration remained constant at all dilutions). The resulting "compound" plate contained serial dilutions of six compounds in duplicate. The final row (H) of the assay plate is filled with HBSS buffer alone (H1-H6) or 10 mM unlabeled gabapentin in HBSS (H7-H12) to measure the total or non-specific uptake, respectively.

$^3$H-gabapentin (e.g., 30-50 Ci/mmol) was diluted into HBSS buffer to a final concentration of 4,000 cpm/μl.

HEK-TREx-hLAT1-h4F2hc cells, treated with 2 mM butyrate and tetracycline (or a tetracycline analog) and plated in 96-well plates, were removed from a cell incubator. The growth media was removed from the cells, and the cells were washed twice in room temperature HBSS (100 μl/well/wash) using a 96-well plate washer (Bio Tek ELX405) with an angled buffer dispenser. Alternatively, cells were manually washed with equivalent volumes using a multichannel pipettor. Immediately before the assay was begun, the final 100 μl of wash solution was removed from the cells. 25 μl from the "compound" plate was added to each well of the cell plate. The assay was started by addition of 25 μl of the $^3$H-gabapentin working solution. The plates were incubated at room temperature for 15 minutes. The assay was stopped by washing the cells four times with ice-cold HBSS buffer using a ELX 405 plate washer (100 μl buffer/well/wash).

Scintillation fluid (200 μl) was added to each well, and the plate was covered with a 96-well adhesive plate cover and placed on a shaker for 10 minutes. The plates were counted on a 96-well plate scintillation counter (1450 MicroBeta Scintillation Counter (Wallac)) for 60 sec/well. The data were analyzed using a sigmoidal dose response curve-fitting program (Prism, GraphPad, Inc, San Diego, Calif.; equation: one-site competition).

Example 9

LAT1 Exchange Assay

An exchange assay was developed to determine the ability of a test compound(s) to stimulate the efflux of radiolabeled gabapentin from HEK-TREx-LAT1-4F2hc cells induced to over-express hLAT1. The results are stated as the potency ($EC_{50}$) and efficacy (V max).

The exchange assays were prepared as follows: Compounds were prepared for assay by diluting a 100 mM stock concentration (in DMSO) to the appropriate working concentration. Typically, seven-point dose response curves were prepared starting at a final assay concentration of 1-5 mM and carrying out three-fold dilutions. These dilutions were prepared by making a working "compound" plate that contains a 1× solution of the desired starting concentration of each test compound in duplicate in row A of a V-bottom microtiter plate. Six 3-fold serial dilutions (from row B to G) were made into the HBSS assay buffer (with the appropriate amount of DMSO so that the DMSO concentration remained constant at all dilutions). The resulting "compound" plate contained serial dilutions of six compounds in duplicate. The final row (H) of the assay plate was filled with 5 mM unlabeled gabapentin in HBSS (H1-H6) or HBSS buffer alone (H7-H12) to measure the maximal or background counts released from the cells, respectively.

$^3$H-gabapentin was diluted into HBSS buffer to a final concentration of 2000 cpm/μl. Enough solution was prepared to add 50 μl/well to all wells (final concentration of 100K cpm/well).

HEK-TREx-hLAT1-h4F2hc cells, treated with 2 mM butyrate and tetracycline (or a tetracycline analog) and plated in 96-well plates, were removed from the incubator. The growth media was removed from the cells, and cells were washed twice in room temperature HBSS (100 μl/well/wash) using a 96-well plate washer (Bio Tek ELX405). Alternatively, cells were washed manually with equivalent volumes using a multichannel pipettor. Immediately before the assay was begun, the final 100 μl of wash solution was removed from the cells.

The assay was begun by addition of 50 μl of the $^3$H-gabapentin working solution to each well to load the cells with radiolabeled gabapentin. The plates were incubated at room temperature for 30 minutes. The cells were then washed four times with ice-cold HBSS using a 96-well plate washer (100 μl buffer/well/wash). Using a 96-well pipettor, 50 μl from the "compound" plate was added to each well of the cell plate, and the plate was incubated at room temperature for 90 seconds. A 96-well pipettor was used to remove 25 μl of the supernatant from the cell plate and placed into a new 96-well, white, clear-bottom plate (the "supernatant" plate). Scintillation fluid (200 μl) was added to each well of both plates, and the plates were covered with a 96-well adhesive plate cover and placed on a shaker for 10 minutes.

Plates were counted on a 96-well plate scintillation counter for 60 sec/well. Two sets of plates were counted for each original assay plate (a supernatant plate and a compound plate). The counts from these plates are used to determine the percent of radiolabeled-gabapentin that was effluxed from the cells after test compound addition. Total counts per well (T) were determined first by adding the value from each plate for each corresponding position. For example, the counts from position A1 of the supernatant plate (A1S) were added to the counts from position A1 of the compound plate (A1C) to determine the total counts in well A1 (A1T) of the original assay plate.

Effluxed counts per well (E) were determined by multiplying the values in the supernatant by two to account for the fact that only 25 µl of the 50 µl efflux volume was placed into the supernatant plate. For example, A1S*2=A1E, or total counts effluxed in well A1 of original assay plate. Compound-stimulated efflux (% of total uptake) was determined by dividing the effluxed counts (E) by the total counts (T) for each well and multiplying by 100. For example, [A1E÷A1T]*100=compound-stimulated efflux (% total uptake) for well A1 of the original assay plate. The data were graphed as the average of the compound-stimulated efflux vs. the log of the test concentration. A curve-fitting program such as Prism (GraphPad, San Diego, Calif.) was used to determine the $EC_{50}$ and the Vmax using a Sigmoidal dose-response curve with the following equation: Y=Bottom+(Top−Bottom)/(1+^A((LogEC$_{50}$−X))); X is the logarithm of concentration. Y is the response; Y starts at Bottom and goes to Top with a sigmoid shape.

Example 10

LAT1 Direct Uptake Assay

A direct uptake assay was developed to determine the ability of a test compound(s) to be transported into HEK-TREx-LAT1-4F2hc cells induced to over-express hLAT1. Four concentrations (bracketing the affinity as measured by competition assays) per compound were routinely tested. Non-specific uptake was determined by measuring the uptake into cells not induced to express the transporter (without tetracycline).

Direct uptake assays were prepared as follows: Compounds were prepared for assay by diluting a 100 mM stock concentration (in DMSO or water, depending on compound solubility) to the appropriate working concentration. Typically, four concentrations bracketing the $IC_{50}$ were tested. The highest test concentration for each compound was made in an eppendorf tube and diluted into HBSS. The samples were robustly vortexed and centrifuged for 10 minutes at 13,200 rpm to spin down any precipitate. The supernatant from these samples (~150 µl/well) was carefully removed and placed into six wells of row A (cmpd 1: A1-6; cmpd 2: A7-12) or row E (cmpd 3: E1-6; cmpd 4: E7-12) of a 96-well polypropylene "compound" plate. Three additional 2-fold dilutions were made in the subsequent rows (B-D or F-G) in HBSS. With this set-up, four compounds were tested per plate: four concentrations of each compound in triplicate on cells that have either been induced (A: plus tetracycline) or not induced (B: no tetracycline) to express the transporter.

An internal standard, 50 µM propranolol in 50:50 ethanol:water, was also used.

Several concentrations of the test compounds were diluted into HEK cell extract (prepared from mock incubated and extracted cells as described below) with a final internal standard concentration of 5 µM. Standards of 10, 5, 1, 0.5, 0.1, 0.05, 0.01 and 0.005 µM were typically run for each test compound. (When L-Dopa was used, 0.01% metabisulfate was added to all buffers, extraction solutions and standard curves to minimize oxidation.)

HEK-TREx-hLAT1-h4F2hc cells were treated with 2 mM butyrate plus (columns 1-3 and 7-9) or minus tetracycline (or tetracycline analog; columns 4-6 and 10-12) and plated in 96-well plates. Cells were removed from the incubator, and the growth media was removed from the cells. Cells were washed twice in room temperature HBSS (100 µl/well/wash) using a 96-well plate washer (Bio Tek ELX405). Alternatively, cells were washed manually with equivalent volumes using a multichannel pipettor. Immediately before the assay was begun, the final 100 µl of wash solution was removed from the cells.

The assay was started by using a 96-well pipettor to add 50 µl from the "compound" plate to each well of the HEK-TREx-hLAT1-h4F2hc cell plate. The plate was incubated at room temperature for 10 minutes. The assay was stopped by washing the cells four times with ice-cold HBSS buffer (using an ELX 405 plate washer; 100 µl buffer/well/wash) with an angled buffer dispenser. After the final wash, as much of the wash buffer as possible was removed by aspirating the wells with a probe that can reach the bottom of the wells. Residual salts from the wash buffer can adversely affect the LC-MS-MS by disrupting the LC method or by suppressing the MS signal.

150 µl of a 50:50 ethanol:water solution was added to each well to lyse the cells and extract the test compound. The plate was covered and allowed to sit for 20 min at room temperature to ensure cell lysis. (The 50% ethanol solution was the generic solution for extraction. For compounds soluble in water or other solvents compatible with the LC-MS-MS, such solutions also can be used, although high concentrations of organic solvent can interfere with the LC run). 120 µl of the cell extract was removed from each well and transferred to a fresh 96-well v-bottom polypropylene plate. This plate was covered with an adherent cover (top seal) and centrifuged for 15 min at 5,700 rpm (Allegra 25R centrifuge) at 4° C. to pellet any cell precipitate. 10 µl of the 50 µM propranolol solution was added to each well of a fresh 96-well plate (a plate amenable for sampling in the LC-MS-MS). 90 µl of the supernatant from the centrifuged cell extract was removed and added to the plate containing the 10 µl of propranolol (using the Cybi-well 96-well pipettor). The sample plate was covered with a bubble lid suitable for use with the LC-MS-MS and placed on a plate shaker for 5 to 10 min to mix the sample and the propranolol. The samples were then submitted for LC-MS-MS analysis. The levels of intracellular compound were determined by converting peak area to concentration by extrapolating from the standard curve for each compound. Uptake was expressed as µM/well.

Example 11

Characterization of The HEK-TREx-LAT1-4F2hc Inducible Cell Line

The HEK-TREx-LAT1-4F2hc inducible cell line was characterized for three substrates, gabapentin, L-Dopa, and phenylalanine, using the competition (Ki), exchange (Km, Vmax), and direct uptake assays (Km, Vmax) described above (Examples 8, 9 and 10, respectively).

Figure 10:
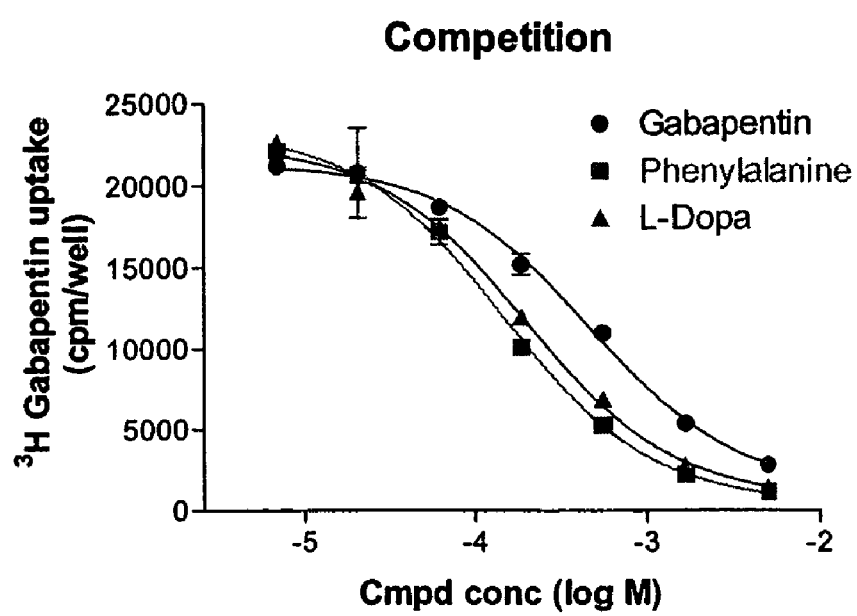
FIG. 10 shows (A) competition assays using HEK-TREx-LAT1-4F2hc cells with $^3$H-gabapentin as a substrate and gabapentin, phenylalanine and L-Dopa as competitors, and (B) a summary of the results in each assay including the assay variability (% error).
Figure 11:
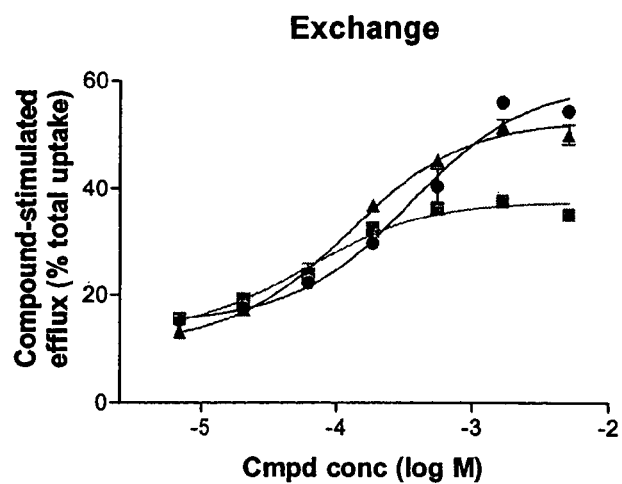
FIG. 11 shows (A) exchange assays using HEK-TREx-LAT1-4F2hc cells with $^3$H-gabapentin as a labeled substrate and gabapentin, phenylalanine and L-Dopa as substrates, and (B) a summary of the results in each assay including the assay variability (% error).

The results of the competition assay are shown in FIG. 10. The results of the exchange assay are shown in FIG. 11. The results of the direct uptake assay are shown in FIG. 12. The data obtained with these assays were compared to results described in the literature, to results obtained internally with oocytes expressing hLAT1 and 4F2hc, and to the results obtained with the KB cell assays. Referring to Table 8 below, in all three of the assay formats, the rank order of affinity (Phe>Dopa>Gabapentin) and of efficacy (Gabapentin>Dopa>Phe) were the same as that observed in other LAT1 systems, specifically, KB cells endogenously expressing LAT1 and oocytes recombinantly expressing LAT1.

TABLE 8

Comparison of the Km or IC50's obtained in various LAT1 assay
Example 12: Uptake of α-Methyl-Dopa

| | $K_m$ or $IC_{50}$ (uM) | | | | | | | |
|---|---|---|---|---|---|---|---|---|
| | Literature | Data | | | | | | |
| | LAT1-expressing oocytes | KB cells | | | HEK-LAT1 cells | | | |
| | Radiolabel Uptake or Competition | Direct Uptake | Competition ($^{14}$C-GP) | Exchange | Direct Uptake | Competition ($^3$H-GP) | Exchange | Direct Uptake |
| Phenylalanine | 12.5-14.2 | 25 | 100 | 36 | 14.5 | 160 | 98 | 140 |
| Gabapentin | 340 | 140 | 210 | 200 | 160 | 400 | 640 | 500 |
| L-Dopa | 34-67 | 66 | 190 | 38 | 60 | 240 | 230 | 230 |

The uptake of α-methyl-Dopa into the HEK-TREx-LAT1-4F2hc inducible cell line was determined at four different concentrations of α-methyl-Dopa, 125, 250, 500 and 1000 µM. Uptake by the LAT1 transporter in induced cells is compared with non-specific uptake by cells not induced to express the transporter (without tetracycline). The results are shown in FIG. 13.

Example 13

Localization of LAT1 in the Human Brain

An anti-LAT1 antibody was used to stain sections of human brain using tissue slides from Lifespan Technologies. To develop antibodies against LAT1, a GST-fusion (glutathion-S-transferase-fusion) protein was synthesized using peptides from the N-terminus of LAT1. The GST-fusion protein was comprised of the glutathion-S-transferase protein bound to a 45 amino acid chain portion of the LAT1 transporter (the 45 amino acids from the N-terminus of LAT1 with the sequence MAGAGPKRRALAAPAAEEKEEAREKM-LAAKSADGSAPAGEGEGVT SEQ ID NO:33. The purified GST-fusion proteins were each injected in rabbits. Specific antibodies were affinity purified from rabbit sera using a column coated with the fusion protein. Paraffin-embedded human brain sections were deblocked, heat treated for antigen retrieval, and stained with the MCT1 antibody and an alkaline-phosphatase conjugated goat anti-rabbit antibody (Jackson Labs). Staining was detected by the DAB colorometric method. The brain sections showed specific staining in brain microvessels.

Although the foregoing compounds, conjugates and methods have been described in detail for purposes of clarity of understanding, it will be obvious that certain modifications may be practiced within the scope of the claim(s) granted herefrom. Unless otherwise apparent from the context, any element, embodiment, or step can be used in combination with any other. All publications and patent documents cited herein are hereby incorporated by reference in their entirety for all purposes to the same extent as if each were so individually denoted.

The invention claimed is:

1. A method of screening an agent, conjugate or conjugate moiety for capacity to be transported through the blood brain barrier, comprising:
   (a) providing a cell expressing a LAT1 transporter, wherein:
   a nucleic acid molecule encoding the LAT1 transporter has been transfected or injected into the cell; and
   the LAT1 transporter is the protein encoded by SEQ ID NO: 1 or has at least 90% sequence identity to the protein encoded by SEQ ID NO:1, and the LAT1 transporter can transport phenylalanine, the LAT1 transporter being situated in the plasma membrane of the cell;
   (b) contacting the cell with an agent, conjugate or conjugate moiety in vitro; and
   (c) determining whether the agent, conjugate or conjugate moiety passes through the plasma membrane via the LAT1 transporter, passage through the plasma membrane via the LAT1 transporter indicating the agent, conjugate or conjugate moiety has capacity to be transported through the blood brain barrier,
   wherein:
   if step (b) comprises contacting the cell with the agent, the agent is a neuropharmaceutical agent or an imaging component;
   if step (b) comprises contacting the cell with the conjugate, the conjugate comprises an agent that is a neuropharmaceutical agent or an imaging component; or
   if step (b) comprises contacting the cells with the conjugate moiety, the method further comprises linking the conjugate moiety to an agent that is a neuropharmaceutical agent or an imaging component.

2. The method of claim 1, wherein the cell also expresses a 4F2HC protein.

3. The method of claim 1, wherein the cell is an oocyte.

4. The method of claim 1, wherein the determining is performed by a competition assay.

5. The method of claim 1, wherein the determining is performed by an exchange assay.

6. The method of claim 1, wherein the determining is performed by a direct uptake assay.

7. The method of claim 1, wherein the cell is a human embryonic kidney (HEK) cell.

8. The method of claim 1, wherein the cell is transformed with an SV40 large T antigen that can be expressed in a temperature sensitive fashion.

9. The method of claim 1, wherein the determining step determines that the agent, conjugate or conjugate moiety passes through the plasma membrane via the LAT1 transporter; and the method further comprises:
   (d) modifying the agent, conjugate or conjugate moiety; and
   (e) determining if the modified agent, conjugate or conjugate moiety is transported with a higher $V_{max}$ by the LAT1 transporter than the agent, conjugate or conjugate moiety.

10. The method of claim 1, wherein the neuropharmaceutical agent is a cytotoxic neuropharmaceutical agent selected from the group consisting of platinum, nitrosourea, nitroimidazole, and nitrogen mustard.

11. The method of claim 1, wherein the agent, conjugate or conjugate moiety comprises an amino acid.

12. The method of claim 11, wherein the amino acid is selected from the group consisting of tryptophan, leucine, methionine, phenylalanine, bicyclohexane amino acid, L-dopa, gabapentin, and baclofen.

13. The method of claim 1, further comprising:
   (d) providing a cell expressing at least one efflux transporter;
   (e) contacting the cell with the agent, conjugate or conjugate moiety in vitro;
   (f) determining that the agent, conjugate or conjugate moiety is transported by to the protein encoded by SEQ ID NO:1 at least one efflux transporter selected from the group consisting of the P-glycoprotein transporter, the multidrug resistance protein transporter, and the breast cancer resistance protein transporter; and
   determining the efflux transporter activity of the agent, conjugate or conjugate moiety.

14. The method of claim 13, further comprising:
   (g) determining the LAT1 transporter activity of the agent, conjugate or conjugate moiety;
   (h) modifying the agent, conjugate or conjugate moiety;
   (i) establishing that the modified agent, conjugate or conjugate moiety retains LAT1 activity; and
   determining the LAT1 transporter activity of the modified agent, conjugate or conjugate moiety;
   (k) determining the efflux transporter activity of the modified agent, conjugate or conjugate moiety; and
   (l) comparing the ratio of LAT 1 activity to the ratio of efflux transporter activity for the agent, conjugate or conjugate moiety and the ratio of LAT1 transporter activity to the efflux transporter activity of the modified agent, conjugate or conjugate moiety wherein an increased ratio of LAT1 activity to efflux transporter activity demonstrates that the modification improves the capacity of the agent, conjugate or conjugate moiety to be transported through the blood brain barrier.

15. The method of claim 13 or 14, wherein the efflux transporter activity is determined by conducting an assay selected from the group consisting of:
   (a) an efflux transporter ATPase activity assay;
   (b) an efflux transporter competition assay; and
   (c) a direct efflux transport assay across a polarized monolayer of cells.

16. The method of claim 13 or 14, wherein the efflux transporter activity is the $V_{max}$ for the efflux transporter.

17. The method of claim 14, wherein the LAT1 transporter activity is the $V_{max}$ for the LAT1 transporter.

18. A method of using the LAT1 transporter to identify an agent or conjugate having the capacity to be transported through the blood brain barrier, comprising:
(a) providing a cell expressing the LAT1 transporter, wherein:
   a nucleic acid molecule encoding the LAT1 transporter has been tranfected or injected into the cell; and
   the LAT1 transporter in the protein encoded by SEQ ID NO:1 or has at least 90% sequence identity thereto, and the LAT1 transporter can transport phenylalanine, the LAT1 transporter being situated in the plasma membrane of the cell;
(b) contracting the cell with an agent, conjugate or conjugate moiety in vitro;
(c) determining that the agent or conjugate is a substrate for the LAT1 transporter; and
(d) determining that the agent or conjugate is actively transported by the LAT1 transporter; transport by the LAT1 transporter indicating that the agent or conjugate has has capacity to be transported through the blood brain barrier.

* * * * *

UNITED STATES PATENT AND TRADEMARK OFFICE
CERTIFICATE OF CORRECTION

PATENT NO. : 7,462,459 B2  Page 1 of 1
APPLICATION NO. : 11/027767
DATED : December 9, 2008
INVENTOR(S) : Noa Zerangue It is certified that error appears in the above-identified patent and that said Letters Patent is hereby corrected as shown below:

Col. 53, Line 16, following the word "for" insert --the--
Col. 53, Line 34, following the word "has" insert --the--

Col. 54, Line 34, following the word "by" insert --the--
Col. 54, Line 34-35, delete "to the protein encoded by SEQ ID NO:1"

Col. 54, Line 45, following the word "LAT1" insert --transporter--
Col. 54, Line 45, delete "and"
Col. 54, Line 46, before the word "determining" insert --(j)--
Col. 54, Line 50, following the word "LAT 1" insert --transporter--
Col. 54, Line 55, following the word "LAT 1" insert --transporter--

Col. 55, Line 10, delete "in" and insert --is--
Col. 55, Line 10, delete "has" and insert --the--
Col. 55, Line 11, delete "thereto" and insert --to the protein encoded by SEQ ID NO:1--

Signed and Sealed this

Seventeenth Day of March, 2009

JOHN DOLL
*Acting Director of the United States Patent and Trademark Office*

SEQUENCE LISTING

<160> NUMBER OF SEQ ID NOS: 33

<210> SEQ ID NO 1
<211> LENGTH: 6327
<212> TYPE: DNA
<213> ORGANISM: Homo sapiens

<400> SEQUENCE: 1

```
cggcggcggc gcgaccgagc atcctggcgg cgccgggcca ctgggagagt ttatgtggcc        60
gaggcagaca agtggaatta ggccttgctg caggggactt catttccttc tcagtactgg       120
acccatttat gaggaggtgg cttatgaaag tgtgatgttc gcgtatttct tgacaggcca       180
cagcaaacac aggtgtgcag gaaccgtttg tcatggaagc cagggagcct gggggggccca       240 cacccaccta ccatcttgtc cctaacacca gccagtccca ggtggaagaa gatgtcagct       300
cgccacctca aaggtcctcc gaaactatgc agctgaagaa ggagatctcc ctgctgaatg       360
gggtcagcct ggtggtgggc aacatgatcg gctcaggat ctttgtctca cccaagggtg       420
tgctggtaca cactgcctcc tatggatgt cactgattgt gtgggccatt ggtgggctct       480
tctctgttgt gggtgcccett tgttatgcag agctgggac caccatcacc aagtcgggag       540
ccagctacgc ttatattcta gaggcctttg ggggcttcat tgccttcatc cgcctgtggg       600
```

```
tctcactgct agttgttgag cccaccggtc aggccatcat cgccatcacc tttgccaact    660
acatcatcca gccgtccttc cccagctgtg atcccccata cctggcctgc cgtctcctgg    720
ctgctgcttg catatgtctg ctgacatttg tgaactgtgc ctatgtcaag tggggcacac    780
gtgtgcagga cacgttcact tacgccaagg tcgtagcgct cattgccatc attgtcatgg    840
gccttgttaa actgtgccag ggacactctg agcactttca ggacgccttt gagggttcct    900
cctgggacat gggaaacctc tctcttgccc tctactctgc cctcttctct tactcaggtt    960
gggacaccct taattttgta acagaagaaa tcaaaaaccc agaaagaaat ttgcccttgg   1020
ccattgggat ttctatgcca attgtgacgc tcatctacat cctgaccaat gtggcctatt   1080
acacagtgct gaacatttca gatgtcctta gcagtgatgc tgtggctgtg acatttgctg   1140
accagacgtt tggcatgttc agctggacca tccccattgc tgttgccctg tcctgctttg   1200
ggggcctcaa tgcatccatc tttgcttcat caaggttgtt cttcgtgggc tcccgggagg   1260
gccacctacc ggaccttctg tccatgatcc acattgagcg ttttacacct atccctgctt   1320
tactgttcaa ttgcaccatg gcactcatct acctcatcgt ggaggatgtt ttccggctta   1380
tcaactactt cagcttcagc tactggttct tcgtgggcct gtctgttgtt ggacagctct   1440
acctccgctg gaaggagccc aagcggcccc ggcctctcaa gctgagcgtg ttttccccca   1500
tcgtgttctg catatgctcc gtgtttctgg tgatagtgcc cctcttcact gacaccatta   1560
attccctcat tggcatcggg attgcccttt ctggagtccc tttctacttc atgggtgttt   1620
acctgccaga gtcccggagg ccattgttta ttcggaatgt cctggctgct atcaccagag   1680
gcacccagca gctttgcttt tgtgtcctga ctgagcttga tgtagccgaa gaaaaaaagg   1740
atgagaggaa aactgactag aggtcagagg tggctttctg aggcctggaa ggcaggccaa   1800
ccagcaaaat cctgataaca agactctgtg ggcccaactc tcctgaatta aaggagcctt   1860
ttgacccaat catatagtgg ggctcagggc cagtgctcac tcttattggt aagctatagg   1920
agactcagga tctgggccaa cctcaaggtg ggggcttcag agggtggggg aagattggg    1980 gaacgggggg aatggtcatt tagtttttact cctgataggt agatgcagct cttacagata   2040
tttacttggt aaagtgcagt ggggaagagg gaatgctagg ttgatagggc tggtggcctc   2100
tgaatttggt atttgaacta ggagtcccta tagaggggct gctttatggg aagttttttct  2160 ctgaccaggt acaacacctg actttaaagg cctgaaatgc taccatttct tcctctggct   2220
caaaattctt ccctggggag agagttatat tcccttattt attgatattt agtccagaac   2280
accagttcta acgaagcatg cgtgtctctt catctacagg atgcaatagg ctgattgtat   2340
ttaaaaatca aagtacccaa aactgagtcc ctttgggctc agaaatgtct gtggtattgg   2400
gtcagactct gaccacagat tttatgctgt ttagcacaat ttctattgag tcttacctgc   2460
aacaatgaac cttaaagatt tttttactca cgtacctgtt acactttagc atacagatag   2520
atcatagatc acgttacaag cacttggctc aggtccagca aggacagatg aacaaattcc   2580
tgagtcagaa gtctgttaat attgctgttt tgaaggacaa tccttttattt tacttgagac  2640 cttacatctt tgttctagct gacagtaaat ctctgggttt ctgttacgaa ctctaagagg   2700
gctgaaactt ctgatattca ggtggatcac ctgaattctc tcagctgtca atggcttgga   2760
gaacatctca tgggcccaag tcatcaaata acctgttcct ctctgtaagg gcagtgtgag   2820
ggactgctgt gcagacccaa gcaatcccaa cctggtgcta ggtcatttca cttttctgaa   2880
aacctcacat caggctgcat cctcttctgt ccctggcacc aggctttgtt tacacttgga   2940
gccaccttgg tgtgggtcac cgggacagtg tactcctctc ctgccagcct cccttcccc    3000
```

```
gaggtgtggt ggctgcagtc tctggaagag cttggtactt gtggggactt ctgttttctc    3060
cctgtggaga tcagtgaaga ctgggaggaa agctgcttca acctgagtcc ggctcttcag    3120
caggctgcac aagtggaagc aactaattct ggtgctcagg ctgggctctc cacccaagtt    3180
aggcctgctc tggcctaatg gatcttactg tatgagcagg acggctgcat tggattgtac    3240
aactgttttg tgatgccccc agacactgtc atcctaggcc gagaagaacc tgctagcttg    3300
acatacccca tgggcttatc cttaggtttt ggaattggtc aacagtgagg cagtctccct    3360
tcctgaccat tcttctccac ccagtcacag ataagggaat aaccttggcc atatatttgc    3420
tcaataaaga ttgaaggaag catggtcata gttgccctgg gttcagagca taatgcatat    3480
gtgaagcatg gggtgacatt cctactgtca tgggtttggg atttgtaacg gcaaattcct    3540
gcccgacgac agggtgtctt atgcaaaggc tgacttgcct gaacgctaag aacatgactt    3600
ctgtctgagc taagctggca cccatcccag ggctcctctg gagctaatcc tttaagcaaa    3660
atgtgcttgc cttttaaaga tccctgaccc cagctttagc tttctccacc agataaccag    3720
ctaatcccag gaatttgctg cccccccacca gtggcttcta gggaaagcaa ggacctcaca    3780
tgccaggtgc cctagtactt gcttagtgag ccatgtcatc ctcctttcat ttttggatgg    3840
tgacagcatt tttcccctct gtgctggata cagacttctc ccaggatcct ctctttggga    3900
gcgaagccag aggatccctca cagcactcaa gcttcatggt ggaattaatt tctgccagct    3960
ctttgttgtc tgtctcctta aatccttttc ctggtgtgct tattatccct tttgcagtga    4020
gtacagttta ttaagttgtc agcccttaaa tattggggaa acttaatgag tataaatagc    4080
agggagcaca ttgtaacagc acagtgtttt gttttttttca cccggttgct gtatgagaat    4140
ggctttcaat cctttgtttc tatgcctaca gacagaaagc aagatgtcta atattagaca    4200
tacaagttgc tgcctgttat aacggtgaat tatacctttg tgcatgccta ggatgtttgt    4260
tgttttaatt agctgcaata tatacggcct gtgtacacag aatttaatca ctgcggcagg    4320
ttgaacaact ccatgtagat aagagcaagt gtaggcaaag gtttagaaaa tggacataaa    4380
gtcaaagaat gatggcaggt aggatgaagg agagatactt aggaaatcct aaaagaggcg    4440
gcaagaaggt acctccctgt gtaactcacc ttcccccatg acagtgagta agagacactc    4500
acaggctatg agggtacacc cctagctgaa tgttctgtgt tgtttcctta gacctgtggt    4560
gtccgctgca acagctacta gccacgtgta gctaattaca ttaaaatgaa ataaaattaa    4620
aagctcagtt tctcagttgc gctaatcaca tttcaagtgc tcagcagcca cccgtgtcta    4680
ctactacaca gtgcagacac agaacatatc atcactgcag atagttctac tggacaatgt    4740
tacgctagaa taaacaccaa ggcagtcagt taaggcagct atggtttgga aaggcatacg    4800
gacagagtct gcttagaaga gatacaagtt gttaataaaa ttgatcctgt tgatagtagt    4860 ttgttttttgt ggtgggtgct gtgaagagta acattactc agtggaaagc taagttcaga    4920
aggtactttg ttttccctcc cttgccttaa gtccttggta tttataatca atgctgaacc    4980
ttctatttca ctaccgctcc ctgttttaga tattcagatt taaaggtttt caaagaatt    5040 actttcttcc atgttcaaag ctagatttta ctaaacacat gtatcacatt catatatatt    5100
gtttcttggc cccactgcca aaggaagtca gtcagtaatt tcacaaccgt tatcagagtt    5160
tggaagcaga aatagctgtt aactaaaatc tcccactgct cagactactt tctgccctaa    5220
tggccattac tatccagtct gtattgctac aagggaccca ctggtacccc ttttagattc    5280
tatcaaaagg aacagggttt tcctagaggc aggcagcctg tgggtatggc acagcagaag    5340
```

```
cttactgcta atgaaatggg aacctccccc cccttgtgg tttcagcaca gaacctgaat    5400
gccaggaaaa attcctgggc caagaagcta aagctaaaga aaccttcctt ttttcaacgt    5460
ttttttttct ttcaaactgt agggtcactt ttgattgagg caagggggtc ctactgtaag    5520
tggaaaagac tcactcccct aacataagtt ttcactgtgt gggatggtg ccgcccgata    5580 tgcttgatat gcttttcctt ccacatgtta agctaggaaa cctaacagga tgtcagcagg    5640
gcagttaact ctggactcag agccctcaag ggcatgtggc agaacctcat ggacatcaca    5700
agaccatcag tctgaatcca ggtcgtgggg gctgtcatag ccgaactcct tctgcacatc    5760
cagagggtac ttgctccaca tccgctgtct gctgctgcct ctttcctcct cactcaggct    5820
gttgtagtca gcagagccta aatgacatc ccgggagtgg attctaaatg tgattttcct    5880
aggctactgc aggagcccct tctcttctca gaaaggtctg tttttgttcc cgattgtaat    5940
gcaaaatcct tgctcaataa ataaaaaaga atatagaatt ctttttttttt taaagaagga    6000 atcactttcc tatcatctaa accaagttcc ttcacactgg agtattttgt cacttctccc    6060
ctccgtggag tattttgtca cttctcccct ccgtatagga ttttttgttg ttgtaagagt    6120
tgtagtcata ttgtaaatat ttttgtacct ttctccttt aacgtgttat tgacaaacct    6180
ccccaaaaga atatgcaatt gtttgattca tttctctgtt atcagacacc aataaattct    6240
ttttgttggg aaaaaaaaaa aaaaaaaaaa aaaaaaaaaa aaaaaaaaaa aaaaaaaaaa    6300 aaaaaagaa aaaaaaaaa aaaaaaa                                        6327

<210> SEQ ID NO 2
<211> LENGTH: 1879
<212> TYPE: DNA
<213> ORGANISM: Homo sapiens

<400> SEQUENCE: 2
ctgcgcggag gcacagaggc cggggagagc gttctgggtc cgagggtcca ggtagggtt      60 gagccaccat ctgaccgcaa gctgcgtcgt gtcgccggtt ctgcaggcac catgagccag    120
gacaccgagg tggatatgaa ggaggtggag ctgaatgagt tagagcccga gaagcagccg    180
atgaacgcgg cgtctggggc ggccatgtcc ctggcggag ccgagaagaa tggtctggtg    240
aagatcaagg tggcggaaga cgaggcggag gcggcagccg cggctaagtt cacgggcctg    300
tccaaggagg agctgctgaa ggtggcaggc agccccggct gggtacgcac ccgctgggca    360
ctgctgctgc tcttctggct cggctggctc ggcatgcttg ctggtgccgt ggtcataatc    420
gtgcgagcgc cgcgttgtcg cgagctaccg gcgcagaagt ggtggcacac gggcgccctc    480
taccgcatcg gcgaccttca ggccttccag ggccacggcg cgggcaacct ggcgggtctg    540
aaggggcgtc tcgattacct gagctctctg aaggtgaagg gccttgtgct gggtccaatt    600
cacaagaacc agaaggatga tgtcgctcag actgacttgc tgcagatcga ccccaatttt    660
ggctccaagg aagattttga cagtctcttg caatcggcta aaaaaagag catccgtgtc    720 attctggacc ttactcccaa ctaccggggt gagaactcgt ggttctccac tcaggttgac    780
actgtgccca caaggtgaa ggatgctctg agttttggc tgcaagctgg cgtggatggg    840
ttccaggttc gggacataga gaatctgaag gatgcatcct cattcttggc tgagtggcaa    900
aatatcacca agggcttcag tgaagacagg ctcttgattg cggggactaa ctcctccgac    960
cttcagcaga tcctgagcct actcgaatcc aacaaagact tgctgttgac tagctcatac   1020
ctgtctgatt ctggttctac tggggagcat acaaaatccc tagtcacaca gtatttgaat   1080
gccactggca atcgctggtg cagctggagt ttgtctcagg caaggctcct gacttccttc   1140
```

```
ttgccggctc aacttctccg actctaccag ctgatgctct tcaccctgcc agggacccct   1200
gttttcagct acggggatga gattggcctg gatgcagctg cccttcctgg acagcctatg   1260
gaggctccag tcatgctgtg ggatgagtcc agcttccctg catcccagg ggctgtaagt    1320 gccaacatga ctgtgaaggg ccagagtgaa gaccctggct ccctcctttc cttgttccgg   1380
cggctgagtg accagcggag taaggagcgc tccctactgc atggggactt ccacgcgttc   1440
tccgctgggc ctggactctt ctcctatatc cgccactggg accagaatga gcgttttctg   1500
gtagtgctta actttgggga tgtgggcctc tcggctggac tgcaggcctc cgacctgcct   1560
gccagcgcca gcctgccagc caaggctgac ctcctgctca gcacccagcc aggccgtgag   1620
gagggctccc ctcttgagct ggaacgcctg aaactggagc tcacgaagg gctgctgctc    1680 cgcttcccct acgcggcctg acttcagcct gacatggacc cactaccctt ctcctttcct   1740
tcccaggccc tttggcttct gattttctc ttttttaaaa acaaacaaac aaactgttgc     1800
agattatgag tgaaccccca ataggtgtg tttctgcctt caaataaaag tcaccctgc      1860 atggtgaagt cttccctct                                                 1879

<210> SEQ ID NO 3
<211> LENGTH: 26
<212> TYPE: DNA
<213> ORGANISM: Artificial
<220> FEATURE:
<223> OTHER INFORMATION: LAT1 forward primer

<400> SEQUENCE: 3
gaggaggcag aggtcaaggt cagagt                                          26

<210> SEQ ID NO 4
<211> LENGTH: 26
<212> TYPE: DNA
<213> ORGANISM: Artificial
<220> FEATURE:
<223> OTHER INFORMATION: LAT1 reverse primer

<400> SEQUENCE: 4
aaaaacctac agatgggcgt cctcag                                          26

<210> SEQ ID NO 5
<211> LENGTH: 26
<212> TYPE: DNA
<213> ORGANISM: Artificial
<220> FEATURE:
<223> OTHER INFORMATION: LAT2 forward primer

<400> SEQUENCE: 5
gaggctgagt ttgggctgaa ttgtgg                                          26

<210> SEQ ID NO 6
<211> LENGTH: 26
<212> TYPE: DNA
<213> ORGANISM: Artificial
<220> FEATURE:
<223> OTHER INFORMATION: LAT2 reverse primer

<400> SEQUENCE: 6
ggtgcaggct gaaggaatgg gaggaa                                          26

<210> SEQ ID NO 7
<211> LENGTH: 26
<212> TYPE: DNA
```

```
<213> ORGANISM: Artificial
<220> FEATURE:
<223> OTHER INFORMATION: Y+LAT1 forward primer

<400> SEQUENCE: 7
agcctgttct tccccatcgt cttctg                                          26

<210> SEQ ID NO 8
<211> LENGTH: 26
<212> TYPE: DNA
<213> ORGANISM: Artificial
<220> FEATURE:
<223> OTHER INFORMATION: Y+LAT1 reverse primer

<400> SEQUENCE: 8
cgatgccgat gagggagttg atggta                                          26

<210> SEQ ID NO 9
<211> LENGTH: 26
<212> TYPE: DNA
<213> ORGANISM: Artificial
<220> FEATURE:
<223> OTHER INFORMATION: BAT forward primer

<400> SEQUENCE: 9
ttttatttcc aaccgtgcat gctact                                          26

<210> SEQ ID NO 10
<211> LENGTH: 26
<212> TYPE: DNA
<213> ORGANISM: Artificial
<220> FEATURE:
<223> OTHER INFORMATION: BAT reverse primer

<400> SEQUENCE: 10
attcctgagg cccttgcatg tgtgat                                          26

<210> SEQ ID NO 11
<211> LENGTH: 26
<212> TYPE: DNA
<213> ORGANISM: Artificial
<220> FEATURE:
<223> OTHER INFORMATION: LAT-ASC forward primer

<400> SEQUENCE: 11
tcggcatcat cattatcctc actggg                                          26

<210> SEQ ID NO 12
<211> LENGTH: 26
<212> TYPE: DNA
<213> ORGANISM: Artificial
<220> FEATURE:
<223> OTHER INFORMATION: LAT-ASC reverse primer

<400> SEQUENCE: 12
ggggtaaacc acgaaacaca gctcct                                          26

<210> SEQ ID NO 13
<211> LENGTH: 26
<212> TYPE: DNA
<213> ORGANISM: Artificial
<220> FEATURE:
<223> OTHER INFORMATION: Mouse LAT1 forward primer

<400> SEQUENCE: 13
actgccctga aagacacccc tacctg                                          26
```

```
<210> SEQ ID NO 14
<211> LENGTH: 26
<212> TYPE: DNA
<213> ORGANISM: Artificial
<220> FEATURE:
<223> OTHER INFORMATION: Mouse LAT1 reverse primer

<400> SEQUENCE: 14
caaaaagcct cacaaaacag cagacc                                              26

<210> SEQ ID NO 15
<211> LENGTH: 26
<212> TYPE: DNA
<213> ORGANISM: Artificial
<220> FEATURE:
<223> OTHER INFORMATION: Human LAT1 forward primer

<400> SEQUENCE: 15
tgggacgtgg acatgcctca aggata                                              26

<210> SEQ ID NO 16
<211> LENGTH: 26
<212> TYPE: DNA
<213> ORGANISM: Artificial
<220> FEATURE:
<223> OTHER INFORMATION: Human LAT1 reverse primer

<400> SEQUENCE: 16
gggcacacag caccaaggat cacaga                                              26

<210> SEQ ID NO 17
<211> LENGTH: 26
<212> TYPE: DNA
<213> ORGANISM: Artificial
<220> FEATURE:
<223> OTHER INFORMATION: Human GLUT1 forward primer

<400> SEQUENCE: 17
ggggcatgat tggctccttc tctgtg                                              26

<210> SEQ ID NO 18
<211> LENGTH: 26
<212> TYPE: DNA
<213> ORGANISM: Artificial
<220> FEATURE:
<223> OTHER INFORMATION: Human GLUT1 reverse primer

<400> SEQUENCE: 18
aggccgcagt acacaccgat gatgaa                                              26

<210> SEQ ID NO 19
<211> LENGTH: 26
<212> TYPE: DNA
<213> ORGANISM: Artificial
<220> FEATURE:
<223> OTHER INFORMATION: Mouse GLUT1 forward primer

<400> SEQUENCE: 19
cgcccattcc tgtctcttcc taccca                                              26

<210> SEQ ID NO 20
<211> LENGTH: 26
<212> TYPE: DNA
<213> ORGANISM: Artificial
<220> FEATURE:
```

-continued

<223> OTHER INFORMATION: Mouse GLUT1 reverse primer

<400> SEQUENCE: 20
tcatggtgtt tgtgtggccc tcagtg                                    26

<210> SEQ ID NO 21
<211> LENGTH: 26
<212> TYPE: DNA
<213> ORGANISM: Artificial
<220> FEATURE:
<223> OTHER INFORMATION: Rat GLUT1 forward primer

<400> SEQUENCE: 21
gaaccacagg gaaagcaact ctaatc                                    26

<210> SEQ ID NO 22
<211> LENGTH: 26
<212> TYPE: DNA
<213> ORGANISM: Artificial
<220> FEATURE:
<223> OTHER INFORMATION: Rat GLUT1 reverse primer

<400> SEQUENCE: 22
tcgggtcatt atttttcacg tttcca                                    26

<210> SEQ ID NO 23
<211> LENGTH: 26
<212> TYPE: DNA
<213> ORGANISM: Artificial
<220> FEATURE:
<223> OTHER INFORMATION: Human BNP1 forward primer

<400> SEQUENCE: 23 cacccccgc tttcctttat ctccag                                     26

<210> SEQ ID NO 24
<211> LENGTH: 26
<212> TYPE: DNA
<213> ORGANISM: Artificial
<220> FEATURE:
<223> OTHER INFORMATION: Human BNP1 reverse primer

<400> SEQUENCE: 24
ctgctggtag gggagatgtg aagtgg                                    26

<210> SEQ ID NO 25
<211> LENGTH: 26
<212> TYPE: DNA
<213> ORGANISM: Artificial
<220> FEATURE:
<223> OTHER INFORMATION: Mouse BNP1 forward primer

<400> SEQUENCE: 25 acggggaca tcactcagaa ttacat                                     26

<210> SEQ ID NO 26
<211> LENGTH: 26
<212> TYPE: DNA
<213> ORGANISM: Artificial
<220> FEATURE:
<223> OTHER INFORMATION: Mouse BNP1 reverse primer

<400> SEQUENCE: 26
ttcttccttt ttctcccagc cgttag                                    26

```
<210> SEQ ID NO 27
<211> LENGTH: 26
<212> TYPE: DNA
<213> ORGANISM: Artificial
<220> FEATURE:
<223> OTHER INFORMATION: Rat BNP1 forward primer

<400> SEQUENCE: 27
gccacacaca gcacagttca gcctcc                                             26

<210> SEQ ID NO 28
<211> LENGTH: 26
<212> TYPE: DNA
<213> ORGANISM: Artificial
<220> FEATURE:
<223> OTHER INFORMATION: Rat BNP1 reverse primer

<400> SEQUENCE: 28
ggacagcact gggcacaagg gaagac                                             26

<210> SEQ ID NO 29
<211> LENGTH: 26
<212> TYPE: DNA
<213> ORGANISM: Artificial
<220> FEATURE:
<223> OTHER INFORMATION: Mouse GFAP forward primer

<400> SEQUENCE: 29
aggaaattgc tggagggcga agaaaa                                             26

<210> SEQ ID NO 30
<211> LENGTH: 26
<212> TYPE: DNA
<213> ORGANISM: Artificial
<220> FEATURE:
<223> OTHER INFORMATION: Mouse GFAP reverse primer

<400> SEQUENCE: 30
caccatcccg catctccaca gtcttt                                             26

<210> SEQ ID NO 31
<211> LENGTH: 26
<212> TYPE: DNA
<213> ORGANISM: Artificial
<220> FEATURE:
<223> OTHER INFORMATION: Rat GFAP forward primer

<400> SEQUENCE: 31
ggtgggcagg tgaggaagaa atggag                                             26

<210> SEQ ID NO 32
<211> LENGTH: 26
<212> TYPE: DNA
<213> ORGANISM: Artificial
<220> FEATURE:
<223> OTHER INFORMATION: Rat GFAP reverse primer

<400> SEQUENCE: 32
tagcagaggt gacaaggggg ggagtg                                             26

<210> SEQ ID NO 33
<211> LENGTH: 45
<212> TYPE: PRT
<213> ORGANISM: Artificial
<220> FEATURE:
<223> OTHER INFORMATION: N-terminus of LAT1 used in GST fusion protein
```

```
-continued

<400> SEQUENCE: 33

Met Ala Gly Ala Gly Pro Lys Arg Arg Ala Leu Ala Ala Pro Ala Ala
1               5                   10                  15

Glu Glu Lys Glu Glu Ala Arg Glu Lys Met Leu Ala Ala Lys Ser Ala
            20                  25                  30

Asp Gly Ser Ala Pro Ala Gly Glu Gly Glu Gly Val Thr
            35                  40                  45
```